US007985421B2

(12) United States Patent
Davis et al.

(10) Patent No.: US 7,985,421 B2
(45) Date of Patent: *Jul. 26, 2011

(54) SUSTAINED RELEASE FORMULATIONS OF GUAIFENESIN AND ADDITIONAL DRUG INGREDIENTS

(75) Inventors: Robert D. Davis, Arlington, TX (US); Ralph W. Blume, Fort Worth, TX (US); Donald Jeffrey Keyser, Southlake, TX (US)

(73) Assignee: Reckitt Benckiser Inc., Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/158,012

(22) Filed: Jun. 22, 2005

(65) Prior Publication Data

US 2005/0276852 A1    Dec. 15, 2005

Related U.S. Application Data

(63) Continuation of application No. 10/121,706, filed on Apr. 15, 2002, now Pat. No. 6,955,821, which is a continuation-in-part of application No. 09/559,542, filed on Apr. 28, 2000, now Pat. No. 6,372,252.

(51) Int. Cl.
*A61K 9/22* (2006.01)
(52) U.S. Cl. ......... 424/468; 424/452; 424/457; 424/474
(58) Field of Classification Search ................... 424/468
See application file for complete search history.

(56) References Cited

U.S. PATENT DOCUMENTS

| | | |
|---|---|---|
| 2,738,303 A | 3/1956 | Blythe |
| 3,065,143 A | 11/1962 | Christenson et al. |
| 3,362,880 A | 1/1968 | Sampson |
| 3,362,881 A | 1/1968 | Eberhardt et al. |
| 3,458,622 A | 7/1969 | Hill |
| 3,555,151 A | 1/1971 | Kaplan et al. |
| 3,634,584 A | 1/1972 | Poole |
| 3,870,790 A | 3/1975 | Lowey et al. |
| 3,981,984 A | 9/1976 | Signorino |
| 4,122,157 A | 10/1978 | Huber |
| 4,140,755 A | 2/1979 | Sheth et al. |
| 4,167,558 A | 9/1979 | Sheth et al. |
| 4,226,849 A | 10/1980 | Schor |
| 4,248,857 A | 2/1981 | DeNeale et al. |
| 4,248,858 A | 2/1981 | Guley et al. |
| 4,259,314 A | 3/1981 | Lowey |
| 4,308,251 A | 12/1981 | Dunn et al. |
| 4,309,404 A | 1/1982 | DeNeale et al. |
| 4,309,405 A | 1/1982 | Guley et al. |
| 4,357,469 A | 11/1982 | Nahas |
| 4,369,172 A | 1/1983 | Schor et al. |
| 4,389,393 A | 6/1983 | Schor et al. |
| 4,424,235 A | 1/1984 | Sheth et al. |
| 4,540,566 A | 9/1985 | Davis et al. |
| 4,543,370 A | 9/1985 | Porter et al. |
| 4,552,899 A | 11/1985 | Sunshine et al. |
| 4,680,323 A | 7/1987 | Lowey |
| 4,695,464 A | 9/1987 | Alderman |
| 4,699,779 A | 10/1987 | Palinczar |
| 4,704,285 A | 11/1987 | Alderman |
| 4,756,911 A | 7/1988 | Drost et al. |
| 4,795,643 A | 1/1989 | Seth |
| 4,798,725 A | 1/1989 | Patel |
| 4,814,179 A | 3/1989 | Bolton et al. |
| 4,826,688 A | 5/1989 | Panoz et al. |
| 4,834,965 A | 5/1989 | Martani et al. |
| 4,834,984 A | 5/1989 | Goldie et al. |
| 4,851,392 A | 7/1989 | Shaw et al. |
| 4,871,548 A | 10/1989 | Edgren et al. |
| 4,900,557 A | 2/1990 | Dell et al. |

(Continued)

FOREIGN PATENT DOCUMENTS

EP    0409781    1/1991

(Continued)

OTHER PUBLICATIONS

The Physicians' Desk Reference: For Nonprescription Drugs and Dietary Supplements, 20th edition, 1999, Medical Economics Company, Inc, Montvale, NJ USA.*
Lacy et al. Drug Information Handbook. (1999): p. 481-482.*
FDA (Guidance for Industry—Bioavailability and bioequivalence studies for orally administered drug products—General considerations (Oct. 2000).*
Bodmeier, R. et al., "Prolonged Release Multiple-Unit Dosage Forms Based on Water-Soluble Cellulosic Polymers or Aqueous Latexes", Proceed. Intern. Sump. Control. Rel. Bioact. Mater., 18 (1991), Controlled Release Society, Inc.
Bauer et al., "Coated Pharmaceutical Dosage Forms," p. 83 (MedPharm Scientific Publishers 1998).

(Continued)

*Primary Examiner* — Jake M. Vu
(74) *Attorney, Agent, or Firm* — Fitzpatrick, Cella, Harper & Scinto

(57) ABSTRACT

The invention relates to a novel pharmaceutical sustained release formulation of guaifenesin and at least one additional drug ingredient. The formulation may comprise a hydrophilic polymer, preferably a hydroxypropyl methylcellulose, and a water-insoluble polymer, preferably an acrylic resin, in a ratio range of about one-to-one (1:1) to about nine-to-one (9:1), more preferably a range of about three-to-two (3:2) to about six-to-one (6:1), and most preferably in a range of about two-to-one (2:1) to about four-to-one (4:1) by weight. This formulation capable of providing therapeutically effective bioavailability of guaifenesin for at least twelve hours after dosing in a human subject. The invention also relates to a modified release product which has two portions: a first portion having an immediate release formulation of guaifenesin and a second portion having a sustained release formulation of guaifenesin, wherein one or both portions has at least one additional drug ingredient. The modified release product has a maximum guaifenesin serum concentration equivalent to that of an immediate release guaifenesin tablet, and is capable of providing therapeutically effective bioavailability of guaifenesin for at least twelve hours after dosing in a human subject.

12 Claims, 18 Drawing Sheets

U.S. PATENT DOCUMENTS

| | | | |
|---|---|---|---|
| 4,968,508 A | 11/1990 | Oren et al. | |
| 4,971,805 A | 11/1990 | Kitanishi et al. | |
| 4,980,170 A | 12/1990 | Schneider et al. | |
| 4,983,398 A | 1/1991 | Gaylord et al. | |
| 4,990,341 A | 2/1991 | Goldie et al. | |
| 4,994,276 A | 2/1991 | Baichwal et al. | |
| 5,004,613 A | 4/1991 | Radebaugh et al. | |
| 5,032,406 A | 7/1991 | Dansereau et al. | |
| 5,047,248 A | 9/1991 | Calanchi et al. | |
| 5,085,865 A | 2/1992 | Nayak | |
| 5,098,715 A | 3/1992 | McCabe et al. | |
| 5,133,974 A * | 7/1992 | Paradissis et al. | 424/480 |
| 5,164,398 A | 11/1992 | Sims et al. | |
| 5,186,943 A | 2/1993 | Okada et al. | |
| 5,186,963 A | 2/1993 | Howman | |
| 5,200,193 A | 4/1993 | Radebaugh et al. | |
| 5,260,073 A | 11/1993 | Phipps | |
| 5,286,493 A | 2/1994 | Oshlack et al. | |
| 5,292,534 A | 3/1994 | Valentine et al. | |
| 5,326,571 A | 7/1994 | Wright et al. | |
| 5,368,861 A | 11/1994 | Ushimaru et al. | |
| 5,376,384 A | 12/1994 | Eichel et al. | |
| 5,395,626 A | 3/1995 | Kotwal et al. | |
| 5,403,593 A | 4/1995 | Royce | |
| 5,427,799 A | 6/1995 | Valentine et al. | |
| 5,445,829 A | 8/1995 | Paradissis | |
| 5,451,409 A | 9/1995 | Rencher et al. | |
| 5,472,704 A | 12/1995 | Santus et al. | |
| 5,486,364 A | 1/1996 | King et al. | |
| 5,494,681 A | 2/1996 | Cuca et al. | |
| 5,529,791 A | 6/1996 | Deboeck et al. | |
| 5,576,022 A | 11/1996 | Yang et al. | |
| 5,593,694 A | 1/1997 | Hayashida et al. | |
| 5,650,169 A | 7/1997 | Conte et al. | |
| 5,656,296 A | 8/1997 | Khan et al. | |
| 5,662,933 A | 9/1997 | Baichwal et al. | |
| 5,738,874 A | 4/1998 | Conte et al. | |
| 5,773,031 A | 6/1998 | Shah et al. | |
| 5,780,057 A | 7/1998 | Conte et al. | |
| 5,807,580 A | 9/1998 | Luber | |
| 5,840,329 A | 11/1998 | Bai | |
| 5,945,123 A * | 8/1999 | Hermelin | 424/464 |
| 5,968,554 A | 10/1999 | Beiman et al. | |
| 5,993,858 A | 11/1999 | Crison et al. | |
| 6,120,802 A | 9/2000 | Breitenbach et al. | |
| 6,210,710 B1 | 4/2001 | Skinner | |
| 6,217,903 B1 | 4/2001 | Skinner | |
| 6,294,199 B1 * | 9/2001 | Conley et al. | 424/468 |
| 6,312,724 B1 | 11/2001 | Odidi et al. | |
| 6,372,252 B1 | 4/2002 | Blume et al. | |
| 6,475,521 B1 | 11/2002 | Timmins et al. | |
| 6,623,756 B1 | 9/2003 | Wilber et al. | |
| 6,838,094 B2 | 1/2005 | Grimmett et al. | |
| 6,955,821 B2 | 10/2005 | Davis et al. | |
| 2002/0022058 A1 | 2/2002 | Lovercheck | |
| 2002/0142044 A1 | 10/2002 | Vendola | |
| 2003/0012820 A1 | 1/2003 | Upadhyay | |
| 2003/0039691 A1 | 2/2003 | Waterman | |
| 2003/0049318 A1 | 3/2003 | Davis et al. | |
| 2003/0091624 A1 | 5/2003 | Szymczak et al. | |
| 2003/0147952 A1 | 8/2003 | Lim et al. | |
| 2003/0215508 A1 | 11/2003 | Davis et al. | |
| 2004/0018233 A1 | 1/2004 | Davis et al. | |
| 2004/0022851 A1 | 2/2004 | Davis et al. | |
| 2004/0033258 A1 | 2/2004 | Koike | |
| 2004/0156902 A1 | 8/2004 | Lee et al. | |
| 2004/0180085 A1 | 9/2004 | Ohkouchi et al. | |
| 2005/0095288 A1 | 5/2005 | Honea | |
| 2005/0152967 A1 | 7/2005 | Tengler et al. | |

FOREIGN PATENT DOCUMENTS

| | | |
|---|---|---|
| EP | 0 875 245 A2 | 9/1999 |
| GB | 2255344 | 11/1992 |
| JP | 7277962 | 10/1995 |
| WO | WO 87/00044 | 1/1987 |
| WO | 94/06416 A1 | 3/1994 |
| WO | 94/27557 A2 | 12/1994 |
| WO | 95/20946 A1 | 8/1995 |
| WO | 95/28148 A1 | 10/1995 |
| WO | 96/04908 A1 | 2/1996 |
| WO | 97/09042 A1 | 3/1997 |
| WO | 98/05305 A1 | 2/1998 |
| WO | 98/22091 A1 | 5/1998 |
| WO | WO 98/22097 | 5/1998 |
| WO | WO 00/33818 A1 | 6/2000 |
| WO | WO 01/19901 A3 | 3/2001 |

OTHER PUBLICATIONS

Request for Reexamination, filed Apr. 20, 2005, USPN 6,372,252, Issued Apr. 16, 2002.

Welling, P.G., "Oral Controlled Drug Administration: Pharmacokinetic Considerations," Drug Dev. Ind. Pharm., 9, 1185-1225 (1983).

Kim, C., "Pharmacokinetic Considerations in the Design of Controlled Release Dosage Forms," Controlled Release Dosage Form Design, ch. 11 (Technomic Publishing Co., Inc. 2000).

International Search Report dated Aug. 19, 2003 for International Application No. PCT/US03/11500, filed Apr. 15, 2003.

Physicians' Desk Reference: For Nonprescription Drugs and Dietary Supplements 807 (Medical Economics Company, Inc., 20th ed. 1999).

Ansel HC and Popovich NG. Pharmaceutical Dosage Forms and Drug Delivery Systems. Fifth Edition. Lea & Febiger. 1990. p. 64.

Bankser GS and Rhodes CT. Modern Pharmaceutics. Fourth Edition. Marcel Dekker, Inc. 2002. p. 83.

Curriculum Vitae of Peter Anthony Crooks, MSc, PhD, FRPharmS, CSci, CChem, FRSC (Jul. 2006).

United Research Laboratories and Mutual Pharmaceutical Company, Press Release: United Research Laboratories/Mutual Pharmaceutical Company Announce ANDA Filing For Guaifenesin Extended-Release Tablets, 600 mg And 1200 mg (Aug. 18, 2006), at http://www.urlmutual.com/guaifenesin_pr.htm.

Correspondence from E. Brendan Magrab, Esq., Vice President, Intellectual Property, United Research Laboratories, Inc. and Mutual Pharmaceutical Company, Inc. to Michael J. Valentino, President & Chief Executive Officer, Adams Respiratory Therapeutics, Inc., including Exhibits A and B and additional attachments (Aug. 22, 2006), *available at* http://www.urlmutual.com/guaifenesin2.pdf (excluding the additional attachments).

United Research Laboratories and Mutual Pharmaceutical Company, Press Release: United Research Laboratories/Mutual Pharmaceutical Company Formally Notifies Adams Respiratory Therapeutics Of Its ANDA Filing For Guaifenesin Extended-Release Tablets, 600 mg And 1200 mg (Aug. 23, 2006), at http://www.urlmutual.com/guaifenesin_pr08232006.htm.

Correspondence from Joseph M. O'Malley, Jr., Esq., Attorney, Fitzpatrick, Cella, Harper & Scinto to E. Brendan Magrab, Esq., Vice President, Intellectual Property, United Research Laboratories, Inc. and Mutual Pharmaceutical Company, Inc., including attachment (Aug. 31, 2006), *available at* http://www.urlmutual.com/guaifenesin3.pdf.

Correspondence from James D. Veltrop, Attorney, Axinn, Veltrop & Harkrider LLP to Joseph M. O'Malley, Jr., Esq., Attorney, Fitzpatrick, Cella, Harper & Scinto, including attachment (Sep. 6, 2006), *available at* http://www.urlmutual.com/guaifenesin4.pdf .

United Research Laboratories and Mutual Pharmaceutical Company, Press Release: United Research Laboratories/Mutual Pharmaceutical Company Views Legal Response From Adams As Excessive And Disengenuous [sic] Attempt To Delay Competition (Sep. 7, 2006), *at* http://www.urlmutual.com/guaifenesin_pr09072006.htm.

Correspondence from James D. Veltrop, Attorney, Axinn, Veltrop & Harkrider LLP to Dominick A. Conde, Attorney, Fitzpatrick, Cella, Harper & Scinto (Sep. 28, 2006), *available at* http://www.urlmutual.com/guaifenesin6.pdf.

Declaration of Harry G. Brittain, Ph.D. (Sep. 28, 2006), *available at* http://www.urlmutual.com/guaifenesin7.pdf.

United Research Laboratories and Mutual Pharmaceutical Company, Press Release: Independent Expert Confirms View That Adams Has No Legal Basis For Pursuing Legal Action Against Mutual Pharmaceutical Company For Its Guaifenesin Extended-Release Tablets, 600 mg And 1200 mg (Sep. 28, 2006), at http://www.urlmutual.com/guaifenesin_pr09282006.htm.

*Adams Respiratory Therapeutics, Inc.* v. *Pharmaceutical Holdings Corp.*, Complaint for Patent Infringement and Certification Pursuant to Local Rule 11.2, including Exhibit A (D.N.J. Oct. 2, 2006).

*Adams Respiratory Therapeutics, Inc.* v. *Pharmaceutical Holdings Corp.*, Complaint for Patent Infringement, including Exhibit A (E.D. Pa. Oct. 4, 2006).

*Adams Respiratory Therapeutics, Inc.* v. *Pharmaceutical Holdings Corp.*, Answer and Counterclaims (E.D. Pa. Oct. 10, 2006).

*Adams Respiratory Therapeutics, Inc.* v. *Pharmaceutical Holdings Corp.*, Defendants' Motion for Summary Judgment (E.D. Pa. Oct. 17, 2006).

*Adams Respiratory Therapeutics, Inc.* v. *Pharmaceutical Holdings Corp.*, Defendants' Memorandum of Law in Support of a Motion for Summary Judgment (E.D. Pa. Oct. 17, 2006).

United Research Laboratories and Mutual Pharmaceutical Company, Press Release: Mutual Pharmaceutical Company Files Counter Suit Against Adams Respiratory Therapeutics (Oct. 17, 2006), at http://www.urlmutual.com/guaifenesin8.pdf.

Gudipati, M., In Vitro/In Vivo Correlation Approach For The Development Of Drug Delivery Systems, Chapter 4, pp. 76-199 (University of Texas at Austin, Aug. 1990).

U.S. Department of Health and Human Services, Approved Drug Products with Therapeutic Equivalence Evaluations, pp. ix-x (19th ed. 1999).

The Merck Index, p. 812 (Merck Research Laboratories, 13th ed. 2001).

*Adams Respiratory Therapeutics, Inc., et al.* v. *Perrigo Company, et al.*, Defendants' First Supplemental Responses and Objections To Adams' Second Set of Interrogatories (Nos. 13-14) (W.D. Mich. Jun. 30, 2009).

*Adams Respiratory Therapeutics, Inc., et al.* v. *Perrigo Company, et al.*, Expert Report of Walter G. Chambliss—Redacted (W.D. Mich. Aug. 10, 2009).

*Adams Respiratory Therapeutics, Inc., et al.* v. *Perrigo Company, et al.*, Rule 26 Expert Report of John T. Goolkasian, Esq. (W.D. Mich. Aug. 4, 2009).

*Adams Respiratory Therapeutics, Inc., et al.* v. *Perrigo Company, et al.*, Expert Report of Michael Mayersohn, Ph.D. (W.D. Mich. Aug. 7, 2009).

*Adams Respiratory Therapeutics, Inc., et al.* v. *Perrigo Company, et al.*, Responsive Expert Report of Dr. Gordon Amidon—Redacted (W.D. Mich. Sep. 18, 2009).

*Adams Respiratory Therapeutics, Inc., et al.* v. *Perrigo Company, et al.*, Responsive Expert Report of Dr. Thomas S. Foster—Redacted (W.D. Mich. Sep. 18, 2009).

*Adams Respiratory Therapeutics, Inc., et al.* v. *Perrigo Company, et al.*, Expert Report of Charles E. Van Horn (W.D. Mich. Sep. 18, 2009).

*Adams Respiratory Therapeutics, Inc., et al.* v. *Perrigo Company, et al.*, Reply Expert Report of Walter G. Chambliss, Ph.D.—Redacted (W.D. Mich. Oct. 9, 2009).

*Adams Respiratory Therapeutics, Inc., et al.* v. *Perrigo Company, et al.*, Reply Expert Report of John T. Goolkasian, Esq. (W.D. Mich. Oct. 7, 2009).

*Adams Respiratory Therapeutics, Inc., et al.* v. *Perrigo Company, et al.*, Reply Expert Report of Michael Mayersohn, Ph.D.—Redacted (W.D. Mich. Oct. 8, 2009).

*Adams Respiratory Therapeutics, Inc., et al.* v. *Perrigo Company, et al.*, Supplemental Expert Report of Dr. Gordon Amidon—Redacted (W.D. Mich. Nov. 14, 2009).

*Adams Respiratory Therapeutics, Inc., et al.* v. *Perrigo Company, et al.*, Second Supplemental Expert Report of Dr. Gordon Amidon—Redacted (W.D. Mich. Nov. 15, 2009).

J.B. Aluri & S. Stavchansky, "Determination of Guaifenesin in Human Plasma by Liquid Chromatography in the Presence of Pseudoephedrine," J. of Pharm. & Biomed. Analysis 11(9):803-808 (1993) PGFSN 053048-053055.

Gordon L. Amidon et al., "Estimating Human Oral Fraction Dose Absorbed: A Correlation Using Rat Intestinal Membrane Permeability for Passive and Carrier-Mediated Compounds," Pharm. Research 5(10):651-654 (1988).

Gordon L. Amidon et al., "Effects of Gravity on Gastric Emptying, Intestinal Transit, and Drug Absorption," J. Clin. Pharmacol. 31:968-973 (1991).

Gordon L. Amidon et al., "A Theoretical Basis for a Biopharmaceutic Drug Classification: The Correlation of in Vitro Drug Product Dissolution and in Vivo Bioavailability," Pharm. Research 12(3):413-420 (1995).

Howard C. Ansel et al., Pharmaceutical Dosage Forms and Drug Delivery Systems 213-225 (6th ed. 1995).

Howard C. Ansel et al., Pharmaceutical Dosage Forms and Drug Delivery Systems 229-243 (7th ed. 1999).

A. Arancibia et al., "Pharmacokinetics and Bioavailability of a Controlled Release Amoxicillin Formulation," Int'l J. of Clin. Pharmacol., Therapy and Toxicology 25(2):97-100 (1987).

B. Huet De Barochez et al., "Influence of Drug Solubility in the Formulation of Hydrophilic Matrices," Drug Development and Industrial Pharmacy 15(14-16):2197-2212 (1989).

Joeby Bass et al., "An Evaluation of the Effect of Food on the Oral Bioavailability of Sustained-Release Morphine Sulfate Tablets (ORAMORPH SR) After Multiple Doses," J. Clin. Pharmacol. 32(11):1003-1007 (1992).

Henning H. Blume & Barbara S. Schug, "The Biopharmaceutics Classification System (BCS): Class III Drugs—Better Candidates for BA/BE Waiver?" European J. Pharm. Sciences 9:117-121 (1999) PGFSN 054720-054726.

Rudolph H. Blythe, "The Formulation and Evaluation of Sustained Release Products," Drug Standards 26(1):1-7 (1958) PGFSN 053162-053170.

Gerald W. Bottenfield et al., "Safety and Tolerability of a New Formulation (90mg/kg/day Divided Every 12 h) of Amoxicillin/Clavulanate (Augmentin®) in the Empiric Treatment of Pediatric Acute Otitis Media Caused by Drug-Resistant *Streptococcus pneumoniae*," Pediatr. Infect. Dis. J. 17(10):963-968 (1998).

Harold G. Boxenbaum, "Physiological and Pharmacokinetic Factors Affecting Performance of Sustained Release Dosage Forms," Drug Dev. & Industrial Pharmacy 8(1):1-25 (1982).

David E. Bugay & W. Paul Findlay, Pharmaceutical Excipients 289 (1999).

Xianhua Cao et al., "Permeability Dominates in Vivo Intestinal Absorption of P-gp Substrate with High Solubility and High Permeability," Molecular Pharmaceutics 2(4):329-340 (2005).

Rong-Kun Chang & Joseph R. Robinson, "Sustained Drug Release from Tablets and Particles Through Coating," in Pharmaceutical Dosage Forms, vol. 3, pp. 199-302 (Herbert A. Lieberman et al. eds., 2d ed., revised and expanded, 1990).

Jun Chen et al., "Superporous Hydrogels as a Platform for Oral Controlled Drug Delivery," in Handbook of Pharmaceutical Controlled Release Technology 211-224 (Donald L. Wise et al. eds. 2000).

Charles S. L. Chiao & Joseph R. Robinson, "Sustained-Release Drug Delivery Systems," in Remington: The Science and Practice of Pharmacy 1660-1675 (Alfonso R. Gennaro ed., 19th ed. 1995).

Yie W. Chien, Novel Drug Delivery Systems 747-776 (2d ed., revised and expanded, 1992).

Ferenc Csizmadia et al., "Prediction of Distribution Coefficient from Structure. 1. Estimation Model," J. Pharm. Sciences 86(7):865-871 (1997).

S. S. Davis et al., "Transit of Pharmaceutical Dosage Forms Through the Small Intestine," Gut 27:886-892 (1986).

J.G. Devane et al., "Pharmacokinetic and In-Vitro Characteristics of Sustained Release Verapamil Products," Drug Development and Industrial Pharmacy 16(7):1233-1248 (1990).

John Devane, "Oral Drug Delivery Technology: Addressing the Solubility/Permeability Paradigm," Pharm. Tech. 22(11):68-80 (1998).

John G. Devane & John G. Kelly, "Effect of Food on the Bioavailability of a Multiparticulate Sustained-Release Verapamil Formulation," Advances in Therapy 8(1):48-53 (1991).

M. R. Dobrinska & P. G. Welling, "Blood Levels from a Sustained-Release Dosage Form," J. Pharm. Sciences 17(10):1728-1729 (1998).

J.B. Dressman et al., "Physicochemical Model for Dose-Dependent Drug Absorption," J. Pharm. Sciences 73(9):1274-1279 (1984).

J.B. Dressman et al., "Absorption Potential: Estimating the Fraction Absorbed for Orally Administered Compounds," J. Pharm. Sciences 74(5):588-589 (1985).

Natalie D. Eddington et al., "Development and Internal Validation of an In Vitro—In Vivo Correlation for a Hydrophilic Metoprolol Tartrate Extended Release Tablet Formulation," Pharm. Research 15(3):466-473 (1998).

M. El-Khawas et al., "Phenylpropanolamine Controlled-Release Tablets," Pharm. Ind. 55(4):392-395 (1993) PGFSN 052986-052991.

Mark G. Eller & Andrew A. Della-Coletta, "Absence of Effect of Food on Alprazolam Absorption from Sustained Release Tablets," Biopharmaceutics & Drug Disposition 11:31-37 (1990).

David Fleisher et al., "Drug, Meal and Formulation Interactions Influencing Drug Absorption After Oral Administration," Clin. Pharmacokinetics 36(3):233-254 (1999) PGFSN 05682-054705.

Arthur C. Guyton & John E. Hall, Textbook of Medical Physiology 793-802, 833-844 (9th ed. 1996).

Lester I. Harrison, "Kinetics of Absorption of a new Once-a-Day Formulation of Theophylline in the Presence and Absence of Food," J. Pharm. Sciences 82(6):644-648 (1993).

A. K. Hilton & P. B Deasy, "In Vitro and In Vivo Evaluation of an Oral Sustained-Release Floating Dosage Form of Amoxycillin Trihydrate," Int'l J. Pharmaceutics 86:79-88 (1992).

A.K. Hilton & P.B. Deasy, "Use of Hyroxypropyl Methylcellulose Acetate Succinate in an Enteric Polymer Matrix to Design Controlled-Release Tablets of Amoxicillin Trihydrate," J. Pharm. Sciences 82(7):737-743 (1993).

J. Hirtz, "The Gastrointestinal Absorption of Drugs in Man: A Review of Current Concepts and Methods of Investigation," Br. J. Clin. Pharmac. 19:77S-83S (1985).

Ammon Hoffman et al., "Pharmacodynamic and Pharmacokinetic Rationales for the Development of an Oral Controlled-Release Amoxicillin Dosage Form," J. Controlled Release 54:29-37 (1998).

H. E. Huber et al., "Utilization of Hydrophilic Gums for the Control of Drug Release from Tablet Formulations I. Disintegration and Dissolution Behavior," J. Pharm. Sciences 55(9):974-976 (1966).

*Adams Respiratory Therapeutics, Inc., et al. v. Perrigo Company, et al.*, Defendants' Reply Memorandum In Support Of Their Motion For Summary Judgment Of Non-Infringement (W.D. Mich. Dec. 28, 2009).

*Adams Respiratory Therapeutics, Inc., et al. v. Perrigo Company, et al.*, Opinion [regarding Plaintiffs' motion for reconsideration and Defendants' motion for summary judgment] (W.D. Mich. Feb. 11, 2010).

*Adams Respiratory Therapeutics, Inc., et al. v. Perrigo Company, et al.*, Order Reconsidering and Vacating In Part Opinion and Order Regarding Claim Construction (W.D. Mich. Mar. 3, 2010).

*Adams Respiratory Therapeutics, Inc., et al. v. Perrigo Company, et al.*, Non-Confidential Brief Of Plaintiffs-Appellants Adams Respiratory Therapeutics, Inc., Adams Respiratory Operations, Inc., and Adams Respiratory Products, Inc. (Fed. Cir. Mar. 24, 2010).

*Reckitt Benckiser Inc. v. Watson Laboratories, Inc.*—Florida & Watson Pharmaceuticals, Inc., Amended Complaint For Patent Infringement (S.D. Fla. Oct. 23, 2009).

*Reckitt Benckiser Inc. v. Watson Laboratories, Inc.*—Florida & Watson Pharmaceuticals, Inc., Defendants Watson Laboratories, Inc.—Florida and Watson Pharmaceuticals, Inc.'s Answer and Counterclaims To Plaintiffs Amended Complaint (S.D. Fla. Oct. 29, 2009).

*Reckitt Benckiser Inc. v. Watson Laboratories, Inc.*—Florida & Watson Pharmaceuticals, Inc., Reckitt Benckiser's Answer to Watson Laboratories, Inc.—Florida and Watson Pharmaceuticals, Inc.'s Oct. 29, 2009 Counterclaims (S.D. Fla. Nov. 23, 2009).

Physicians' Desk Reference to Pharmaceutical Specialties and Biologicals, passim (46th ed. 1992) PGFSN 054207-054265.

Physicians' Desk Reference to Pharmaceutical Specialties and Biologicals, passim (50th ed. 1996) PGFSN 054266-054360.

Physicians' Desk Reference to Pharmaceutical Specialties and Biologicals, passim (51st ed. 1997) PGFSN 054361-054442.

Physicians' Desk Reference to Pharmaceutical Specialties and Biologicals, passim (52d ed. 1998) PGFSN 054443-054508.

Physicians' Desk Reference to Pharmaceutical Specialties and Biologicals, passim (53d ed. 1999) PGFSN 054509-054572.

Random House Unabridged Dictionary 1780 (2d ed. 1993).

Textbook of Therapeutics: Drug and Disease Management 1255 (Eric T. Herfindal & Dick R. Gourley eds., 6th ed. 1996) PGFSN 054880-054882.

The United States Pharmacopeia / The National Formulary 19-20, 724-725 (USP 23/ NF 18 1995) PGFSN 054594-054599.

Webster's New World/Stedman's Concise Medical Dictionary 345 (1987).

Wilson and Gisvold's Textbook of Organic Medicinal and Pharmaceutical Chemistry 948-956 (John H. Block & John M. Beale, Jr. eds.,11th ed. 2004) PGFSN 054738-054748.

The Dow Chemical Company, Formulating Sustained Release Pharmaceutical Products With Methocel (1982).

Thomson Reuters Press Release, "Thomson Healthcare Launches PDRhealth.com" pp. 1-3 (Nov. 5, 2007) (found at http://thomsonreuters.com/content/press_room/tsh/mdx_ThomHcareLaunchesPDRhealth on Mar. 31, 2010).

47 FR 30002-30010 (Jul. 9, 1982) PGFSN 053860-053880.

54 FR 8494-8509 (Feb. 28, 1989) ART 0489984-0489999 & PGFSN 053881-053916.

Food and Drug Administration, Compliance Program Guidance Manual, Program 7361.003, Chapter 61—OTC Drug Evaluation (May 2007).

Food and Drug Administration, Inspections, Compliance, Enforcement, and Criminal Investigations, CPG Sec. 450.200 Drugs—General Provisions and Administrative Procedures for Recognition as Safe and Effective (CPG 7132b.15) (found at fda.gov/ICECI/.../ucm074388.htm on Oct. 15, 2009).

U.S. Department of Health and Human Services, Food and Drug Administration, Center for Devices and Radiological Health, Guidance for Industry and FDA Staff, "Format for Traditional and Abbreviated 510(k)s" (Aug. 12, 2005).

U.S. Department of Health and Human Services, Food and Drug Administration, Center for Drug Evaluation and Research (CDER), Guidance for Industry, "Extended Release Oral Dosage Forms: Development, Evaluation, and Applications of In Vitro/In Vivo Correlations" (Sep. 1997).

U.S. Department of Health and Human Services, Food and Drug Administration, Center for Drug Evaluation and Research (CDER), Guidance for Industry, "SUPAC-MR: Modified Release Solid Oral Dosage Forms, Scale-Up and Postapproval Changes: Chemistry, Manufacturing, and Controls; In Vitro Dissolution Testing and In Vivo Bioequivalence Documentation" (Sep. 1997).

U.S. Department of Health and Human Services, Food and Drug Administration, Center for Drug Evaluation and Research (CDER), Guidance for Industry, "Waiver of In Vivo Bioavailability and Bioequivalence Studies for Immediate Release Solid Oral Dosage Forms Containing Certain Active Moieties/Active Ingredients Based on a Biopharmaceutics Classification System," Draft Guidance (Jan. 1999) PGFSN 054706-054719.

U.S. Department of Health and Human Services, Food and Drug Administration, Center for Drug Evaluation and Research (CDER), Guidance for Industry, "Statistical Approaches to Establishing Bioequivalence" (Jan. 2001).

U.S. Department of Health and Human Services, Food and Drug Administration, Center for Drug Evaluation and Research (CDER), Guidance for Industry, "Food-Effect Bioavailability and Fed Bioequivalence Studies" (Dec. 2002).

U.S. Department of Health and Human Services, Food and Drug Administration, Center for Drug Evaluation and Research (CDER), Guidance for Industry, "Power Blends and Finished Dosage Units—Stratified In-Process Dosage, Unit Sampling and Assessment," Draft Guidance (Oct. 2003).

U.S. Department of Health and Human Services, Food and Drug Administration, Center for Drug Evaluation and Research (CDER), Guidance for FDA Staff and Industry, "Marketed Unapproved Drugs—Compliance Policy Guide, Sec. 440.100 Marketed New Drugs Without Approved NDAs or ANDAs" (Jun. 2006).

Correspondence from David J. Horowitz, Esq., Director, Office of Compliance, Center for Drug Evaluation and Research, Food and Drug Administration to 45 entities, Guaifenesin single product Warning Letters (Oct. 11, 2002).
Correspondence from David J. Horowitz, Esq., Director, Office of Compliance, Center for Drug Evaluation and Research, Food and Drug Administration to 26 entities, Guaifenesin multiple products Warning Letters (Oct. 11, 2002).
Correspondence from Salomon Stavchansky Ph.D., Professor of Pharmaceutics and Alcon Centennial Professor of Pharmacy to R. Andrew Morgan, R.Ph., Adams Laboratories, Inc., Regulatory Affairs, including attachment (Feb. 1, 1994) ART 0447100-0447152.
STN Search Report 1-5 (Oct. 7, 2009).
*Adams Respiratory Therapeutics, Inc.*, et al. v. *Perrigo Company*, et al., Plaintiffs' Opening Memorandum of Law on Claim Construction (W. D. Mich. May 21, 2009).
*Adams Respiratory Therapeutics, Inc.*, et al. v. *Perrigo Company*, et al., Declaration of Dr. Thomas Foster (W.D. Mich. May 21, 2009).
*Adams Respiratory Therapeutics, Inc.*, et al. v. *Perrigo Company*, et al., Defendants' Markman Brief In Support of Their Proposed Claim Construction (W.D. Mich. May 21, 2009).
*Adams Respiratory Therapeutics, Inc.*, et al. v. *Perrigo Company*, et al., Declaration of Walter G. Chambliss, Ph.D. (W.D. Mich. May 20, 2009).
*Adams Respiratory Therapeutics, Inc.*, et al. v. *Perrigo Company*, et al., Plaintiffs' Responsive Memorandum of Law On Claim Construction (W.D. Mich. Jun. 22, 2009).
*Adams Respiratory Therapeutics, Inc.*, et al. v. *Perrigo Company*, et al., Supplemental Declaration of Dr. Thomas Foster (W.D. Mich. Jun. 22, 2009).
*Adams Respiratory Therapeutics, Inc.*, et al. v. *Perrigo Company*, et al., Defendants' Responsive Brief to Plaintiffs' Opening Memorandum of Law On Claim Construction (W.D. Mich. Jun. 22, 2009).
*Adams Respiratory Therapeutics, Inc.*, et al. v. *Perrigo Company*, et al., Plaintiffs' Reply Memorandum of Law On Claim Construction (W. D. Mich. Jul. 8, 2009).
*Adams Respiratory Therapeutics, Inc.*, et al. v. *Perrigo Company*, et al., Second Supplemental Declaration of Dr. Thomas Foster (W.D. Mich. Jul. 8, 2009).
*Adams Respiratory Therapeutics, Inc.*, et al. v. *Perrigo Company*, et al., Defendants' Reply In Support of Defendants' Markman Brief in Support of Their Proposed Claim Construction (W.D. Mich. Jul. 8, 2009).
*Adams Respiratory Therapeutics, Inc.*, et al. v. *Perrigo Company*, et al., Supplemental Declaration of Walter G. Chambliss, Ph.D. (W.D. Mich. Jul. 7, 2009).
*Adams Respiratory Therapeutics, Inc.*, et al. v. *Perrigo Company*, et al., Order and Proposed Construction of Disputed Terms (W.D. Mich. Jul. 24, 2009).
*Adams Respiratory Therapeutics, Inc.*, et al. v. *Perrigo Company*, et al., Submission in Response To The Court's Proposed Construction of Disputed Terms (W.D. Mich. Aug. 7, 2009).
*Adams Respiratory Therapeutics, Inc.*, et al. v. *Perrigo Company*, et al., Defendants' Response To The Court's Jul. 24, 2009 Proposed Construction of Disputed Terms (W.D. Mich. Aug. 7, 2009).
*Adams Respiratory Therapeutics, Inc.*, et al. v. *Perrigo Company*, et al., Order Adopting Proposed Claim Construction (W.D. Mich. Aug. 24, 2009).
*Adams Respiratory Therapeutics, Inc.*, et al. v. *Perrigo Company*, et al., Memorandum in Support of Plaintiffs' Motion For Reconsideration of Court's Aug. 24, 2009 Order Regarding Claim Construction of The Term "Fully Bioavailable in The Subject's Stomach"—Redacted (W.D. Mich. Dec. 4, 2009).
*Adams Respiratory Therapeutics, Inc.*, et al. v. *Perrigo Company*, et al., Defendants' Opposition to Plaintiffs' Motion For Reconsideration of the Court's Aug. 24, 2009 Order Construing The Term "Fully Bioavailable in The Subject's Stomach"—Redacted (W.D. Mich. Dec. 14, 2009).
*Adams Respiratory Therapeutics, Inc.*, et al. v. *Perrigo Company*, et al., Defendants' Memorandum In Support of Their Motion For Summary Judgment of Non-Infringement—Redacted (W.D. Mich. Nov. 16, 2009).

*Adams Respiratory Therapeutics, Inc.*, et al. v. *Perrigo Company*, et al., Plaintiffs' Memorandum of Law In Opposition To Defendants' Motion For Summary Judgment of Non-Infringement—Redacted (W. D. Mich. Dec. 14, 2009).
A. S. Hussain et al., "The Biopharmaceutics Classification System: Highlights of the FDA's Draft Guidance," Dissolution Technologies May 1999 Article #1, pp. 1-4 and Biopharmaceutics Classification Figures 1-3, pp. 1-2 (found at http://www.dissolutiontech.com/DTresour/599articles/Biopharm_Class2_copy.html and http://www.dissolutiontech.com/DTresour/599articles/BiopharmFig1-3.html on Oct. 15, 2009).
L. Kalantzi et al., "Biowaiver Monographs for Immediate Release Solid Oral Dosage Forms: Acetaminophen (Paracetamol)," J. Pharm. Sciences 95(1):4-14 (2006).
Lydia C. Kaus et al., "The Effect of In Vivo Dissolution, Gastric Emptying Rate, and Intestinal Transit Time on the Peak Concentration and Area-Under-the Curve of Drugs with Different Gastrointestinal Permeabilities," Pharm. Research 16(2):272-280 (1999).
Th. Knapp, "Der Einfluss von Guajakolderivaten auf die Ausscheidung der Glukuronsäure," J. Suisse de Chimie et Pharmacie LX(17):229-231, 245-248, 257-262 (1911), with certified translation.
Leszek Krowczynski, Extended-Release Dosage Forms 4-6, 51-58 (Dorota Porebska Brozyna trans. 1987).
C. Gordon Law, "Dose Proportionality," in Encyclopedia of Biopharmaceutical Statistics 295-297 (Shein-Chung Chow ed., 2d ed., revised and expanded, 2003).
Mark A. Longer & Joseph R. Robinson, "Sustained-Release Delivery Systems," in Remington's Pharmaceutical Sciences 1644-1661 (Alfonso R. Gennaro ed., 17th ed. 1985).
R. D. Maier, "Zum Nachweis von Guaiphenesin, einem Inhaltsstoff einiger Rezeptfreier Schlafmittel," Archives of Toxicology 45:123-131 (1980) PGFSN 054573-054583.
Carol N. Manners et al., "Distribution Coefficient, a Convenient Term for the Relation of Predictable Physico-Chemical Properties to Metabolic Processes," Xenobiotica 18(3):331-350 (1988) PGFSN 054769-054790.
Marilyn N. Martinez & Gordon L. Amidon, "A Mechanistic Approach to Understanding the Factors Affecting Drug Absorption: A Review of Fundamentals," J. Clin. Pharmacol. 42:620-643 (2002).
William R. Maynard, Jr. & Robert B. Bruce, "GLC Determination of Guaiacol Glyceryl Ether in Blood," J. Pharm. Sciences 59(9):1346-1348 (1970) PGFSN 054808-054811.
Hussain Y. Mohammed & Frederick F. Cantwell, "Liquid Chromatographic Analysis of Pharmaceutical Syrups Using Pre-Columns and Salt-Adsorption on Amberlite XAD-2," Analytical Chemistry 50(3):491-496 (1978) PGFSN 054812-054817.
Sakae Obara et al, "Evaluation of Several Grades of Hydroxypropyl Methylcellulose for Use in a Sustained-Release Tablet Matrix," Advances in Pharmaceutics and Pharm. Tech., pp. 212-219 (1989).
Rebecca L. Oberle & Gordon L. Amidon, "The Influence of Variable Gastric Emptying and Intestinal Transit Rates on the Plasma Level Curve of Cimetidine; An Explanation for the Double Peak Phenomenon," J. Pharmacokinetics & Biopharmaceutics 15(5):529-544 (1987).
Eugene L. Parrott, "Solid Dosage Forms," in Prescription Pharmacy, Dosage Formulation and Pharmaceutical Adjuncts 103-162 (Joseph B. Sprowls, Jr. ed., 2d ed. 1970) PGFSN 053056-053116.
James E. Polli et al., "Summary Workshop Report: Biopharmaceutics Classification System—Implementation Challenges and Extension Opportunities," J. Pharm. Sciences 93(6):1375-1381 (2004).
W. Steven Pray, Nonprescription Product Therapeutics 225-231 (1999).
Gurvinder Singh Rekhi et al., "Identification of Critical Formulation and Processing Variables for Metoprolol Tartrate Extended-Release (ER) Matrix Tablets," J. Controlled Release 59:327-342 (1999).
Manford Robinson et al., "Sustained Action Dosage Forms," in The Theory and Practice of Industrial Pharmacy 439-465 (Leon Lachman et al. eds., 2d ed. 1976) PGFSN 053001-053029.
P. E. Rolan, "The Assessment of Pharmacokinetics in Early Phase Drug Evaluation," in Handbook of Phase I/II Clinical Drug Trials 169-175 (John O'Grady & Pieter H. Joubert eds. 1997).

Earl Rosen & Joseph V. Swintosky, "Preparation of a 35S Labelled Trimeprazine Tartrate Sustained Action Product for Its Evaluation in Man," J. of Pharmacy and Pharmacology, XII Supp.:237T-244T (1960) PGFSN 052992-053000.
Edward M. Rudnic & Mary Kathryn Kottke, "Tablet Dosage Forms," in Modern Pharmaceutics 333, 359-364 (Gilbert S. Banker & Christopher T. Rhodes eds., 3d ed., revised and expanded, 1996).
H. Rupprecht & D. Regensburg, "XIV. Silicium Dioxide and Silicates in Drug Delivery," in Controlled Drug Delivery 197-225 (Bernd W. Müller ed. 1987).
Leroy A. Shervington & Amal Shervington, "Guaifenesin," in Analytical Profiles of Drug Substances and Excipients 121-164 (Harry G. Brittain ed. 1998) PGFSN 054626-054671.
Patrick J. Sinko & Gordon L. Amidon, "Characterization of the Oral Absorption of β-Lactam Antibiotics. I. Cephalosporins: Determination of Intrinsic Membrane Absorption Parameters in the Rat Intestine In Situ," Pharm. Research 5(10) 645-650 (1988).
J. P. Skelly et al., "Scaleup of Oral Extended-Release Dosage Forms," Pharm. Research 10(12):1800-1805 (1993).
Dennis Smith et al., "Design of Drugs Involving the Concepts and Theories of Drug Metabolism and Pharmacokinetics," Medicinal Research Reviews 16(3):243-266 (1996) PGFSN 054600-054625.
Dennis Smith, "Can We Design Drugs with Low Variability," in Variability in Human Drug Response 251-261 (G.T. Tucker ed. 1999) PGFSN 054727-054737.
Dennis Smith & Barry Jones, "Variability in Drug Response as a Factor in Drug Design," Current Opinion in Drug Discovery & Development 2(1):33-41 (1999) PGFSN 054672-054681.
Joel T. Smith & Dutt V. Vinjamoori, "Rapid Determination of Logarithmic Partition Coefficients Between n-Octanol and Water Using Micellar Electrokinetic Capillary Chromatography," J. Chromatography B: Biomed. Applications 669(1):59-66 (1995) PGFSN 054759-054768.
David O. Thueson, Thueson's Guide to Over-The-Counter Drugs 54-57 (1995).
Klara Valkó et al., "Chromatographic Hydrophobicity Index by Fast-Gradient RP-HPLC: A High-Throughput Alternative to log P/log D," Anal. Chem. 69:2022-2029 (1997).
Daniel L. Wagner & Vikram S. Patel, "Steady-State Human Pharmacokinetics and Bioavailability of Guaifenesin and Pseudoephedrine in a Sustained-Release Tablet Relative to Immediate-Release Liquids," Int'l J. Pharmaceutics 114:171-176 (1995) PGFSN 053117-053122.
Zheng Wang et al., "In-Vivo and In-Vitro Evaluations of a Modified-Release Oral Dosage Form of Nifedipine by Hybridization of Hydroxypropyl-β-Cyclodextrin and Hydroxypropylcelluloses in Dogs," J. Pharm. Pharmacol. 46:505-507 (1994) PGFSN 052869-52871.
Hong Gi Yi et al., "Formulation of a Extended Release Tablet Containing Dexibuprofen," Arch. Pharm. Res. 31(12):1637-1643 (2008).
Lawrence X. Yu & Gordon L. Amidon, "A Compartmental Absorption and Transit Model for Estimating Oral Drug Absorption," Int'l J. Pharmaceutics 186:119-125 (1999).
Excipients and Delivery Systems for Pharmaceutical Formulations 123-124, 186-190 (D. R. Karsa & R. A. Stephenson eds. 1995).
Handbook of Pharmaceutical Excipients 252-261, 280-282, 424-427 (Ainley Wade & Paul J. Weller eds., 2d ed. 1994).
Handbook of Pharmaceutical Excipients 188-191 (Raymond C. Rowe et al. eds., 5th ed. 2006).
The Merck Index 716-717 (Susan Budavari et al. eds., 11th ed. 1989) PGFSN 054754-054758.
The Merck Index 776-777 (Susan Budavari et al. eds., 12th ed. 1996) PGFSN 054749-054753.
Pharmaceutical Dosage Forms, vol. 1, pp. 2, 241, 247-284 (Herbert A. Lieberman et al. eds., 2d ed., revised and expanded, 1989).
Pharmaceutical Dosage Forms, vol. 2, pp. 7-11, 13-20, 60-67 (Herbert A. Lieberman et al. eds., 2d ed., revised and expanded, 1990).
Physicians' Desk Reference to Pharmaceutical Specialties and Biologicals 216, 490-491 (5th ed. 1951) PGFSN 053917-053921.
Physicians' Desk Reference to Pharmaceutical Specialties and Biologicals 248, 517, 522, 570 (9th ed. 1955) PGFSN 053922-053927.
Physicians' Desk Reference to Pharmaceutical Specialties and Biologicals, passim (14th ed. 1960) PGFSN 053928-053941.
Physicians' Desk Reference to Pharmaceutical Specialties and Biologicals, passim (25th ed. 1971) PGFSN 053942-053983.
Physicians' Desk Reference to Pharmaceutical Specialties and Biologicals, passim (34th ed. 1980) PGFSN 053984-054044.
Physicians' Desk Reference to Pharmaceutical Specialties and Biologicals, passim (39th ed. 1985) PGFSN 054045-054130.
Physicians' Desk Reference to Pharmaceutical Specialties and Biologicals, passim (40th ed. 1986) PGFSN 054131-054206.
Drituss G and Q-Bid LA, Qualitest 011, produced by Perrigo Company et al. in the *Adams Respiratory Therapeutics, Inc.* et al. v. *Perrigo Company* et al. (W.D. Mich.) litigation in Aug. 2008.
Q-Bid LA label, Qualitest 015, Apr. 1994.
Q-Bid LA label, Qualitest 017, May 1999.
Drituss G and Q-Bid LA, Vintage 011, produced by Perrigo Company et al. in the *Adams Respiratory Therapeutics, Inc.* et al. v. *Perrigo Company* et al. (W.D. Mich.) litigation in Aug. 2008.
Drituss G label, Vintage 012, Dec. 2001.
Drituss G label, Vintage 013, Dec. 2001.
Guaifenesin Long-Acting Tablets, Vintage 014, Dec. 2001.
Q-Bid LA label, Vintage 015, Apr. 1994.
Q-Bid LA label, Vintage 016, Feb. 1999.
Q-Bid LA label, Vintage 017, May 1999.
Guaifenesin Sustained-Release Tablets and Guaifenesin/ Dextromethorphan Hydrobromide Sustained-Release Tablets, Vintage 018, Mar. 2001.
*Adams Respiratory Therapeutics, Inc.*, et al. v. *Perrigo Company*, et al., NonConfidential Brief for Defendants-Appellees (Fed. Cir. Apr. 23, 2010).
*Adams Respiratory Therapeutics, Inc.*, et al. v. *Perrigo Company*, et al., Non-Confidential Reply Brief of Plaintiffs-Appellants (Fed. Cir. May 3, 2010).
*Adams Respiratory Therapeutics, Inc.*, et al. v. *Perrigo Company*, et al., Opinion (Fed. Cir. Aug. 5, 2010).
*Reckitt Benckiser Inc.* v. *Watson Laboratories, Inc.*—Florida, Defendant Watson Laboratories, Inc—Florida's [Redacted] Amended Answer and Counterclaims to Plaintiffs Amended Complaint (S.D. Fla. Aug. 2, 2010).
*Reckitt Benckiser Inc.* v. *Watson Laboratories, Inc.*—Florida & Watson Pharmaceuticals, Inc., Defendant Watson Laboratories, Inc.—Florida's Claim Construction Brief (S.D. Fla. Sep. 10, 2010).
*Reckitt Benckiser Inc.* v. *Watson Laboratories, Inc.*—Florida & Watson Pharmaceuticals, Inc., Declaration of Thomas Dowling, Pharm.D., Ph.D., In Support of Defendant Watson Laboriatories [sic], Inc.—Florida's Claim Construction Brief (S.D. Fla. Sep. 10, 2010).
*Reckitt Benckiser Inc.* v. *Watson Laboratories, Inc.*—Florida & Watson Pharmaceuticals, Inc., Declaration of Gilbert S. Baker Ph.D., D.Sc., In Support of Defendant Watson Laboratories, Inc.—Florida's Claim Construction Brief (S.D. Fla. Sep. 10. 2010).
*Reckitt Benckiser Inc.* v. *Watson Laboratories, Inc.*—Florida, Plaintiffs Opening Memorandum of Law In Support of Its Motion For a Markman Hearing and To Construe Certain Language of The Asserted Claims (S.D. Fla. Sep. 10, 2010).
*Reckitt Benckiser Inc.* v. *Watson Laboratories, Inc.*—Florida, Declaration of Dr. Thomas Foster (S.D. Fla. Sep. 10, 2010).
*Reckitt Benckiser Inc.* v. *Watson Laboratories, Inc.*—Florida, Declaration of Dr. Gordon Amidon (S.D. Fla. Sep. 10, 2010).
*Reckitt Benckiser Inc.* v. *Watson Laboratories, Inc.*—Florida, Plaintiffs Memorandum of Law In Response to Watson's Sep. 10 Markman Brief, Public Version (S.D. Fla. Sep. 24, 2010).
*Reckitt Benckiser Inc.* v. *Watson Laboratories, Inc.* - Florida, Supplemental Declaration of Dr. Gordon Amidon, Public Version (S.D. Fla. Sep. 24, 2010).
*Reckitt Benckiser Inc.* v. *Watson Laboratories, Inc.*—Florida, Supplemental Declaration of Dr. Thomas Foster, Public Version (S.D. Fla. Sep. 24, 2010).
*Reckitt Benckiser Inc.* v. *Watson Laboratories, Inc.*—Florida & Watson Pharmaceuticals, Inc., Defendant Watson Laboratories, Inc.—Florida's Opposition to Plaintiffs Motion for a Markman Hearing and to Construe Certain Language of the Asserted Claims (S.D. Fla. Sep. 24, 2010).

*Reckitt Benckiser Inc.* v. *Watson Laboratories, Inc.*—Florida, Plaintiffs Memorandum of Law In Reply To Watson's Sep. 24 Opposition Markman Brief, Public Version (S.D. Fla. Oct. 1, 2010).

*Reckitt Benckiser Inc.* v. *Watson Laboratories, Inc.*—Florida & Watson Pharmaceuticals, Inc., Defendant Watson Laboratories, Inc.—Florida's Reply In Support of Claim Construction Brief (S.D. Fla. Oct. 1, 2010).

*Reckitt Benckiser Inc.* v. *Watson Laboratories, Inc.*—Florida & Watson Pharmaceuticals, Inc., Declaration of Thomas Dowling, Pharm.D., Ph.D., In Support of Defendant Watson Laboriatories [sic], Inc.—Florida's Claim Construction Brief (S.D. Fla. Oct. 1, 2010).

*Reckitt Benckiser Inc.* v. *Watson Laboratories, Inc.*—Florida, Reckitt Benckiser Inc.'s Reply To Watson Laboratories, Inc.—Florida's Amended Counterclaims (S.D. Fla. Nov. 12, 2010).

*Reckitt Benckiser Inc.* v. *Watson Laboratories, Inc.*—Florida, Order of Partial Dismissal (S.D. Fla. Dec. 6, 2010).

*Reckitt Benckiser Inc.* v. *Watson Laboratories, Inc.*—Florida, Claim Construction Order (S.D. Fla. Jan. 12, 2010).

*Reckitt Benckiser Inc.* v. *Watson Laboratories, Inc.*—Florida, Redacted Findings of Fact and Conclusions of Law (S.D. Fla. Feb. 18, 2011).

*Reckitt Benckiser Inc.* v. *Watson Laboratories, Inc.*—Florida, Non-Confidential Brief on Behalf of Plaintiff-Appellant Reckitt Benckiser, Inc. (Fed. Cir. Mar. 17, 2011).

*Reckitt Benckiser Inc.* v. *Watson Laboratories, Inc.*—Florida, Non-Confidential Brief For Defendant-Appellee Watson Laboratories, Inc.—Florida (Fed. Cir. Apr. 18, 2011).

\* cited by examiner

Dextromethorphan HBr Dissolution Release Rates for Mucinex DM
1200 mg Guaifenesin / 60 mg Dextromethorphan HBr (Mean, Standard Error)

Guaifenesin Plasma Concentrations Following the Administration of 1200 mg Guaifenesin
and 60 mg Dextromethorphan Hydrobromide to Normal Volunteers in Three Formulations
(Mean, Standard Error)

Dextromethorphan Plasma Concentrations Following the Administration of 1200 mg Guaifenesin and 60 mg Dextromethorphan Hydrobromide to Normal Volunteers in Three Formulations (Mean, Standard Error)

Dextrorphan Plasma Concentrations Following the Administration of 1200 mg Guaifenesin and 60 mg Dextromethorphan Hydrobromide to Normal Volunteers in Three Formulations
(Mean, Standard Error)

Pseudoephedrine HCl dissolution Release Rates for Mucinex D
1200 mg Guaifenesin / 120 mg Pseudoephedrine HCl Plasma Guaifenesin Concentration Following Administration of 1200 mg Guaifenesin Along with 120 mg Pseudoephedrine HCl to Normal Volunteers (Mean, Standard Error)

Plasma Pseudoephedrine Concentration Following Administration of 120 mg Pseudoephedrine HCl along with 1200 mg Guaifenesin to Normal Volunteers (Mean, Standard Error)

SUSTAINED RELEASE FORMULATIONS OF GUAIFENESIN AND ADDITIONAL DRUG INGREDIENTS

CROSS-REFERENCE TO RELATED APPLICATIONS

This application is a continuation of U.S. patent application Ser. No. 10/121,706, filed on Apr. 15, 2002, which is a continuation-in-part of U.S. patent application Ser. No. 09/559,542, filed on Apr. 28, 2000, which issued as U.S. Pat. No. 6,372,252 on Apr. 16, 2002. All of the aforementioned applications and patents are hereby incorporated by reference in their entirety.

BACKGROUND OF THE INVENTION

1. Field of the Invention

The present invention is directed to a sustained release formulation for oral administration comprising guaifenesin and at least one drug ingredient and methods of manufacture thereof. In particular, the invention is directed to a sustained release formulation which maintains a therapeutically effective blood concentration of guaifenesin and at least one drug ingredient for a duration of at least twelve hours. The present invention further relates to a modified release bi-layer tablet containing guaifenesin and at least one drug ingredient which demonstrates a maximum serum concentration equivalent to an immediate release tablet yet maintains a therapeutically effective blood concentration of guaifenesin for a duration of about twelve hours.

2. Description of Related Art

Sustained release pharmaceutical formulations provide a significant advantage over immediate release formulations to both clinicians and their patients. Sustained release dosage forms are administered to patients in much fewer daily doses than their immediate release counterparts and generally achieve improved therapeutic effect and efficiency in the fewer daily doses.

For example, in a standard dosage regimen a 400 mg immediate release dosage form of an active ingredient (hereinafter "drug" or "medicament") with a short half-life, such as guaifenesin, may have to be administered to a patient three times within 12 hours to maintain adequate bioavailability of the drug to achieve therapeutic effect. This results in a series of three serum concentration profiles in the patient in which there is a rapid increase of drug followed by a similar rapid decrease. Such rapid increases and decreases provide a patient with a short window of appropriate blood concentration of the medicament for optimum therapy. A 1200 mg sustained release dosage form, on the other hand, may only have to be administered to a patient once every 12 hours to achieve therapeutic effect. Sustained release dosage forms generally control the rate of active drug absorption, so as to avoid excessive drug absorption while maintaining effective blood concentration of the drug to provide a patient with a consistent therapeutic effect over an extended duration of time.

Besides reducing the frequency of dosing and providing a more consistent therapeutic effect, sustained release dosage forms generally help reduce side effects caused by a drug. Because sustained release dosage forms deliver the drug in slow, incremental amounts versus the cyclic high and low concentrations of immediate release formulations, it is easier for a patient's body to digest the drug, thereby avoiding undesirable side-effects. For patients who self-administer therapies, sustained release dosage forms generally result in greater compliance due to the lower frequency of dosing, lower quantity of dosage units to be consumed, and reduced undesired side-effects.

Sustained release formulations for the sequential or timed release of medicaments are well known in the art. Generally, such formulations contain drug particles mixed with or covered by a polymer material, or blend of materials, which is resistant to degradation or disintegration in the stomach and/or in the intestine for a selected period of time. Release of the drug may occur by leeching, erosion, rupture, diffusion or similar actions depending upon the nature of the polymer material or polymer blend used.

Conventionally, pharmaceutical manufacturers have used hydrophilic hydrocolloid gelling polymers such as hydroxypropyl methylcellulose, hydroxypropyl cellulose, or Pullulan to formulate sustained release tablets or capsules. These polymers first form a gel when exposed to an aqueous environment of low pH thereby slowly diffusing the active medicament which is contained within the polymer matrix. When the gel enters a higher pH environment such as that found in the intestines, however, it dissolves resulting in a less controlled drug release. To provide better sustained release properties in higher pH environments, some pharmaceutical manufacturers use polymers which dissolve only at higher pHs, such as acrylic resins, acrylic latex dispersions, cellulose acetate phthalate, and hydroxypropyl methylcellulose phthalate, either alone or in combination with hydrophilic polymers.

Generally, these formulations are prepared by combining the medicament with a finely divided powder of the hydrophilic polymer, or the hydrophilic and water-insoluble polymers. These ingredients are mixed and granulated with water or an organic solvent and the granulation is dried. The dry granulation is then usually further blended with various pharmaceutical additives and compressed into tablets.

Although these types of formulations have been successfully used to manufacture dosage forms which demonstrate sustained release properties, these formulations generally do not have the desired release profile or serum concentration of medicament over an extended period of time. These sustained release formulations generally result in a delay in the appearance of drug in the blood stream, thereby delaying therapeutic effect. Additionally, when the drug does appear, its maximum serum concentration ($C_{max}$) is lower than the maximum concentration required for the most effective therapeutic result. Furthermore, most formulations which claim twelve hour potency release almost all of their drug within six to eight hours, making the formulation less therapeutically effective towards the end of the twelve hour period. To prevent blood serum concentrations of active drug from falling below a therapeutically effective level at extended time periods, many manufacturers increase the drug strength of the dosage form. The increase in drug strength, however, results in a concomitant increase in side-effects.

To improve the release profile of certain sustained release dosage forms, some pharmaceutical manufacturers have made tablets and capsules which comprise a combination of an immediate release formulation and a sustained release formulation. Although this solution improves the $C_{max}$ and length of time before the drug appears in the blood stream in some formulations, the extended therapeutic effect is not improved.

Furthermore, every medicament has different solubility properties and pH dependencies which affect its dissolution rate, and hence its bioavailability. Bioavailability can also be affected by a number of factors such as the amounts and types of adjuvants used, the granulation process, compression forces (in tablet manufacturing), surface area available for dissolution and environmental factors such as agitation in the stomach and the presence of food. Due to these numerous factors, specific formulations play an important role in the preparation of prolonged action solid dosage forms, particularly in the preparation of solid dosage forms which achieve appropriate bioavailability for optimum therapeutic effect.

Guaifenesin is known chemically as 3-(2-methoxyphenoxy)-1,2-propanediol. It is an expectorant, a drug which increases respiratory tract fluid secretions and helps to loosen phlegm and bronchial secretions. By reducing the viscosity of secretions, guaifenesin increases the efficiency of a cough reflex and of ciliary action in removing accumulated secretions from trachea and bronchi. Guaifenesin is readily absorbed from the intestinal tract and is rapidly metabolized and excreted in urine. Guaifenesin has a typical plasma half-life of approximately one hour. Because of the rapid metabolization and excretion of guaifenesin, typical immediate release dosage tablets of guaifenesin provide only a short window of therapeutic effectiveness for patients resulting in the various recognized problems described above.

None of the prior art has described a sustained release dosage form of guaifenesin which is capable of sustaining therapeutic effective for at least twelve hours. Likewise, none of the prior art has described a sustained release dosage form of guaifenesin which has a $C_{max}$ equivalent to that of an immediate release formulation, appears in the blood stream as quickly as an immediate release formulation, yet sustains therapeutic effect for at least twelve hours.

SUMMARY OF THE INVENTION

The present invention overcomes the problems and disadvantages associated with current strategies and designs in formulations of modified release guaifenesin dosage forms.

This invention relates to a novel sustained release pharmaceutical formulation comprising guaifenesin and at least one drug ingredient. The sustained release formulation may comprise a combination of at least one hydrophilic polymer and at least one water-insoluble polymer. The total weight ratio of hydrophilic polymer to water-insoluble polymer may be in a range of about one-to-one (1:1) to about nine-to-one (9:1), more preferably in a range of about three-to-two (3:2) to about six-to-one (6:1), and most preferably in a range of about two-to-one (2:1) to about four-to-one (4:1). When a tablet comprising the sustained release formulation is exposed to an aqueous medium of low pH, such as that found in the stomach, the polymer combination gels causing guaifenesin and the drug ingredient to diffuse from the gel. When the tablet passes to the intestines where an aqueous medium of higher pH is present, the gel begins to dissolve, thereby releasing guaifenesin and the drug ingredient(s) in controlled amounts. The tablet is capable of releasing therapeutically effective amounts of guaifenesin over an extended period, i.e. twelve or more hours and at least one additional drug ingredient immediately, over an extended period, or both.

This invention also encompasses a modified release composition which comprises two discrete portions (e.g. a bi-layer tablet, or capsule), an immediate release formulation and a sustained release formulation. Each formulation comprises a specific quantity of guaifenesin and may optionally contain at least one additional drug. The immediate release formulation is formulated to dissolve in aqueous acidic medium, such as that found in the stomach, to quickly release guaifenesin contained within the portion, and optionally quickly release the at least one additional drug ingredient. The sustained release portion may comprise a combination of hydrophilic polymer and a water-insoluble polymer in a ratio range of about one-to-one (1:1) to about nine-to-one (9:1), more preferably a range of about three-to-two (3:2) to about six-to-one (6:1), and most preferably from about two-to-one (2:1) to about four-to-one (4:1).

The present invention also relates to sustained release preparations of the type described above in the form of capsules having beads or granules of both immediate release formulation and beads or granules of sustained release formulation. Alternatively, the sustained release formulation may comprise a core that is coated by a layer of the immediate release formulation to form a single tablet. For purpose of illustration only, the invention will be described in detail in the context of the bi-layered tablet embodiment.

The bi-layer tablet of the present invention demonstrates a maximum serum concentration ($C_{max}$) and time of availability in the blood stream that are equivalent to an immediate release tablet. The bi-layer tablet also provides sustained release of guaifenesin over at least a twelve hour period from one dose. The bi-layer tablet of the present invention further maintains serum concentration levels of guaifenesin at a therapeutically effective level for at least a twelve hour period without an increase in the drug strength of the dosage form. As the bi-layer tablet of the present invention also contains at least one additional drug ingredient, the additional drug ingredient can be formulated within the sustained release formulation, immediate release formulation, or both. In one embodiment, the bi-layer tablet of the present invention maintains serum concentration levels of at least one additional drug at a therapeutically effective level for at least a twelve hour period without an increase in the drug strength of the dosage form.

The present invention also relates to methods of manufacturing sustained release formulations and bi-layer tablets of the present invention. An example of a manufacturing method for a sustained release formulation comprises mixing a hydrophilic polymer and active ingredients in a mixer, adding water to the mixture and continuing to mix and chop, drying the mixture to obtain hydrophilic polymer encapsulated granules, milling and screening the resulting granulation, and blending it with various pharmaceutical additives, additional hydrophilic polymer, and water insoluble polymer. The formulation may then be tableted and may further be film coated with a protective coating which rapidly dissolves or disperses in gastric juices.

An example of a bi-layer tablet manufacturing method comprises blending a quantity of guaifenesin and optionally, at least one drug ingredient with various excipients, colorants, and/or other pharmaceutical additives to form an immediate release formulation, separately blending another quantity of guaifenesin and at least one drug ingredient with a hydrophilic polymer, a water-insoluble polymer, and various excipients, colorants, and/or other pharmaceutical additives to form a sustained release formulation, and compressing a quantity of the immediate release formulation with a quantity of the sustained release formulation to form a bi-layer tablet. The tablet may then be optionally coated with a protective coating which rapidly dissolves or disperses in gastric juices.

Other objects, advantages and embodiments of the invention are set forth in part in the description which follows, and in part, will be obvious from this description, or may be learned from the practice of the invention.

DETAILED DESCRIPTION OF THE INVENTION

Figure 1:
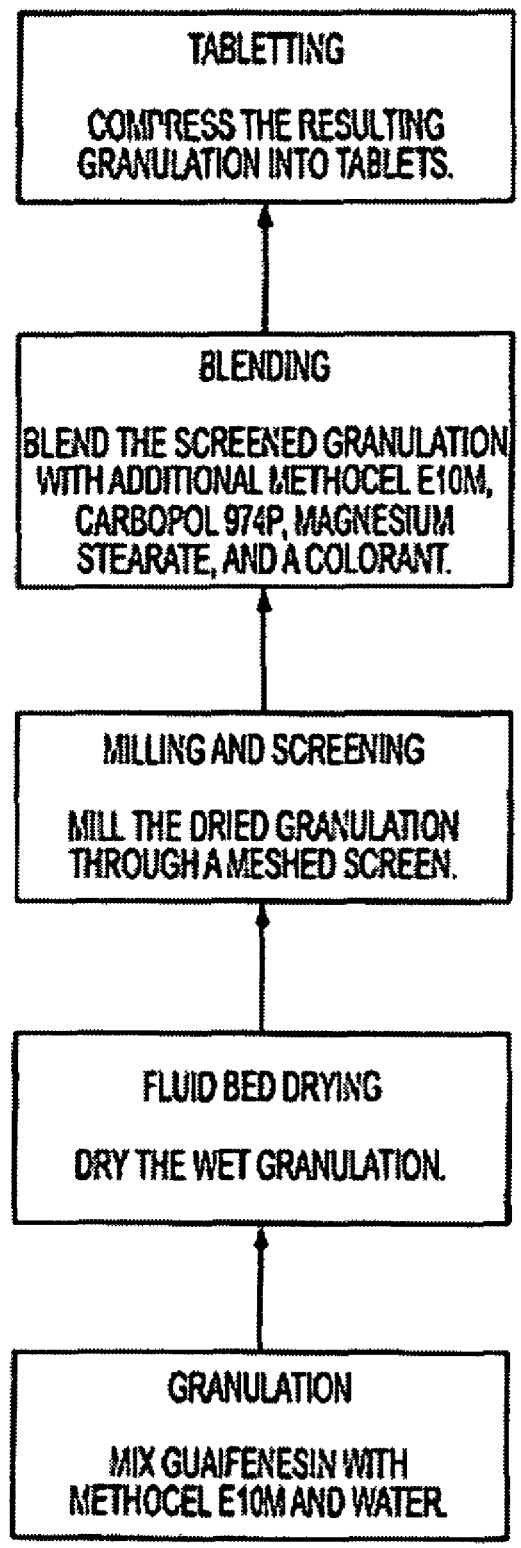
FIG. 1 is a flow diagram depicting steps in a wet granulation method for manufacturing the sustained release formulation of the present invention.
Figure 2:
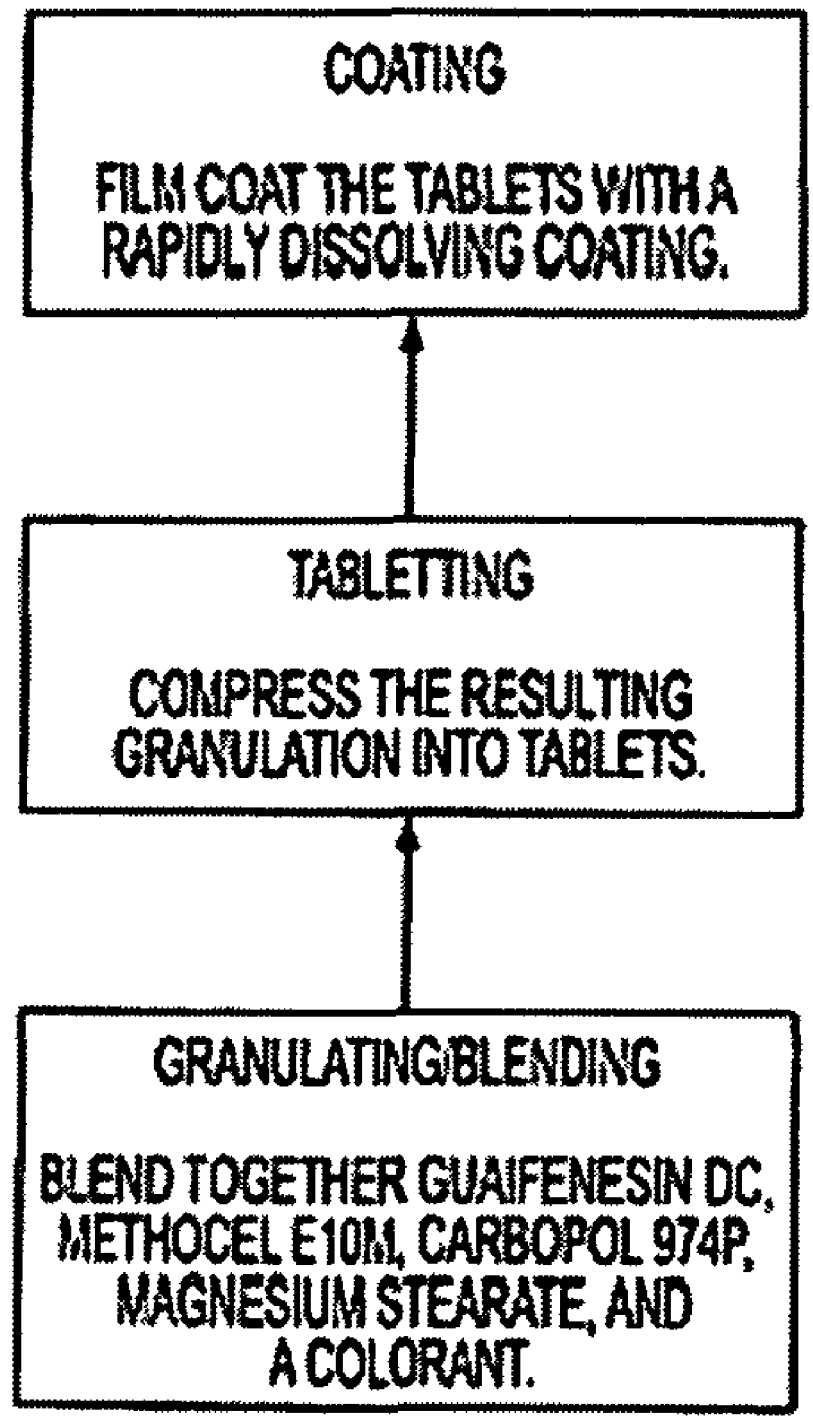
FIG. 2 is a flow diagram depicting steps in a dry granulation method for manufacturing the sustained release formulation of the present invention.
Figure 3:
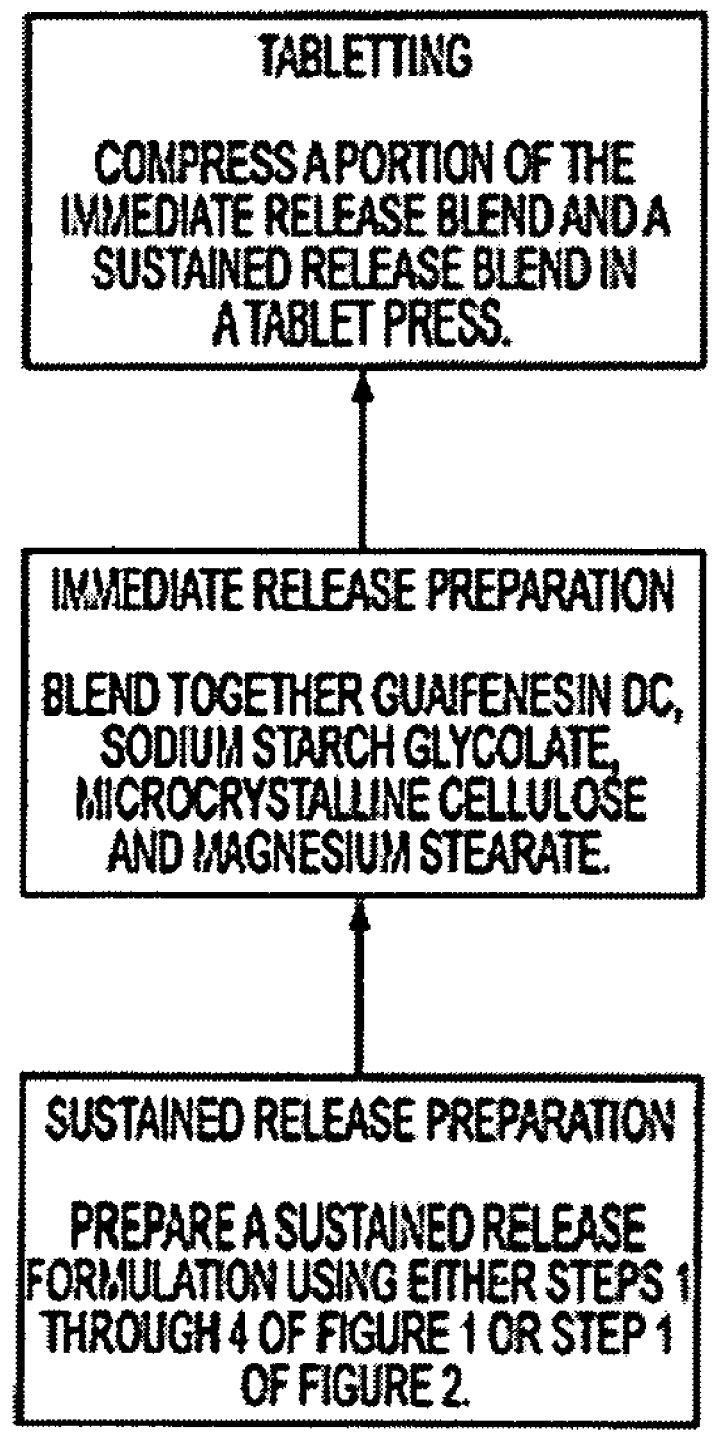
FIG. 3 is a flow diagram depicting steps in a method for manufacturing the bi-layer tablet of the present invention.

The present invention encompasses a novel sustained release formulation comprising guaifenesin and at least one additional drug ingredient. This invention also encompasses a modified release composition which comprises two discrete portions, an immediate release formulation and a sustained release formulation. Each formulation comprises a specific quantity of guaifenesin and may optionally contain at least one additional drug. The immediate release formulation is formulated to dissolve in aqueous acidic medium, such as that found in the stomach, to quickly release guaifenesin contained within the portion, and optionally quickly release the at least one additional drug ingredient. In a preferred embodiment, the sustained release formulation comprises a combination of a hydrophilic polymer and a water-insoluble polymer in a ratio range of about one-to-one (1:1) to about nine-to-one (9:1), more preferably a range of about three-to-two (3:2) to about six-to-one (6:1), and most preferably in a range of about two-to-one (2:1) to about four-to-one (4:1).

The present invention also relates to sustained release preparations of the type described above in the form of bi-layered tablets or capsules having a combination of beads or granules of immediate release formulation and beads or granules of sustained release formulation. Alternatively, the sustained release formulation may comprise a core that is coated by a layer of immediate release formulation to form a single tablet. For purpose of illustration only, the invention will be described in detail in the context of the bi-layered tablet embodiment. When the embodiment is a bi-layered tablet, the tablet is made of two portions: one portion comprising a sustained release formulation and a second portion comprising an immediate release formulation. In a preferred embodiment, the at least one additional drug ingredient can be present within the sustained release formulation, the immediate release formulation, or both depending upon the desired effect.

1. Sustained Release Formulation

In one embodiment of the present invention, a sustained release formulation comprises guaifenesin and at least one drug ingredient both mixed with a polymer blend which comprises at least one hydrophilic polymer and at least one water-insoluble polymer. In a further embodiment, the sustained release formulation may comprise a combination of guaifenesin and at least one additional drug ingredient, wherein the additional drug ingredient includes, but not limited to, an antitussive such as dextromethorphan hydrobromide, codeine, hydrocodone, a decongestant such as phenylephrine hydrochloride, phenylpropanolamine hydrochloride, pseudoephedrine hydrochloride or ephedrine, an antihistamine such as chlorpheniramine maleate, brompheniramine maleate, phenindamine tartrate, pyrilamine maleate, doxylamine succinate, phenyltoloxamine citrate, diphenhydramine hydrochloride, promethazine, and clemastine fumerate, an analgesic such as aspirin, ibuprofen, naprosin, and acetaminophen, or combinations thereof. Preferably, the drug ingredient is dextromethorphan hydrobromide, pseudoephedrine hydrochloride, or a combination thereof.

Hydrophilic polymers suitable for use in the sustained release formulation include: one or more natural or partially or totally synthetic hydrophilic gums such as acacia, gum tragacanth, locust bean gum, guar gum, or karaya gum, modified cellulosic substances such as methylcellulose, hydroxomethylcellulose, hydroxypropyl methylcellulose, hydroxypropyl cellulose, hydroxyethylcellulose, carboxymethylcellulose; proteinaceous substances such as agar, pectin, carrageen, and alginates; and other hydrophilic polymers such as carboxypolymethylene, gelatin, casein, zein, bentonite, magnesium aluminum silicate, polysaccharides, modified starch derivatives, and other hydrophilic polymers known to those of skill in the art or a combination of such polymers.

These hydrophilic polymers gel and dissolve slowly in aqueous acidic media thereby allowing the guaifenesin and at least one drug ingredient to diffuse from the gel in the stomach. When the gel reaches the intestines, it dissolves in controlled quantities in the higher pH medium, where the guaifenesin and the drug ingredient are fairly absorbable, to allow sustained release of guaifenesin and at least one drug ingredient throughout the digestive tract. Preferred hydrophilic polymers are the hydroxypropyl methylcelluloses such as those manufactured by The Dow Chemical Company and known as METHOCEL ethers. In one preferred embodiment of a sustained release formulation the hydrophilic polymer is a METHOCEL ether known as METHOCEL E10M.

Water-insoluble polymers which are suitable for use in the sustained release formulation are polymers which generally do not dissolve in solutions of a pH below 5, and dissolve more slowly in basic solutions than the hydrophilic polymer. Because the polymer is insoluble in low pH environments such as those found in gastric fluid, it aids in retarding drug release in those regions. Likewise, because the polymer dissolves more slowly in solutions of higher pH than hydrophilic polymers, it aids in retarding drug release throughout the intestines. This overall delayed release results in a more uniform serum concentration of guaifenesin.

The water-insoluble polymers suitable for use in this invention include: polyacrylic acids, acrylic resins, acrylic latex dispersions, cellulose acetate phthalate, polyvinyl acetate phthalate, hydroxypropyl methylcellulose phthalate, and other polymers common to those of skill in the art. In a preferred embodiment, a sustained release formulation comprises the acrylic resin CARBOPOL 974P supplied by BF Goodrich.

A sustained release formulation of the present invention may further comprise pharmaceutical additives including, but not limited to: lubricants such as magnesium stearate, calcium stearate, zinc stearate, powdered stearic acid, hydrogenated vegetable oils, talc, polyethylene glycol, and mineral oil; colorants such as Emerald Green Lake and various FD&C colors; binders such as sucrose, lactose, gelatin, starch paste, acacia, tragacanth, povidone polyethylene glycol, Pullulan and corn syrup; glidants such as colloidal silicon dioxide and talc; surface active agents such as sodium lauryl sulfate, dioctyl sodium sulfosuccinate, triethanolamine, polyoxyethylene sorbitan, poloxalkol, and quarternary ammonium salts; preservatives and stabilizers; excipients such as lactose, mannitol, glucose, fructose, xylose, galactose, sucrose, maltose, xylitol, sorbitol, chloride, sulfate and phosphate salts of potassium, sodium, and magnesium; and/or any other pharmaceutical additives known to those of skill in the art. Colorants include, but are not limited to, Emerald Green Lake, FD&C Red #40, FD&C Yellow #6, FD&C Yellow #10, or FD&C Blue #1. In one preferred embodiment, a sustained release formulation further comprises magnesium stearate and Emerald Green Lake. In another preferred embodiment, a sustained release formulation further comprises magnesium stearate and FD&C Blue #1 Aluminum Lake Dye.

A sustained release formulation of the present invention can comprise at least two drug ingredients, at least one hydrophilic polymer, at least one water-insoluble polymer, and at least one pharmaceutical additive in any appropriate percent quantity which permits dissolution of drug ingredients that results in a therapeutically effective serum concentration profile for a full twelve hours. In a preferred embodiment, a sustained release formulation comprises from about 75% to about 95% guaifenesin by weight, from about 1% to about 15% by weight of a additional drug ingredient, from about 1% to about 10% hydroxypropyl methylcellulose, from about 0.5% to about 2.5% acrylic resin, from about 0.4% to about 1.5% magnesium stearate, and from about 0.01% to about 1% colorant by weight. In a more preferred embodiment, a sustained release formulation comprises from about 80% to about 90% guaifenesin by weight, from about 3% to about 10% by weight of a additional drug ingredient, from about 2% to about 5% hydroxypropyl methylcellulose, from about 1% to about 1.5% acrylic resin, from about 0.7% to about 1% magnesium stearate, and from about 0.03% to about 0.13% colorant by weight.

The present inventive sustained release formulation controls release of guaifenesin and at least one additional drug ingredient into the digestive tract slowly over time. The drug guaifenesin experiences a shift in water solubility as the pH of the environment in which it resides (i.e. stomach versus intestinal tract) changes. In a more acidic environment, such as that found in the stomach, guaifenesin is less soluble while in a higher pH environment, such as that found in the intestines, guaifenesin is readily soluble. Dissolution rate of guaifenesin throughout the digestive tract is thus of primary importance in determining concentrations of guaifenesin attained in the blood and tissues as a drug formulation is digested.

To maintain a blood concentration of guaifenesin which provides good therapeutic effect, the release, or dissolution, of guaifenesin from a formulation matrix is preferably retarded and/or controlled through the intestines. The combination of hydrophilic and water-insoluble polymers of the sustained release formulation of the present invention gels when exposed to media of low pH. This creates a matrix out of which guaifenesin can diffuse. When the gelled polymer combination is exposed to media of a higher pH, the gel begins to slowly dissolve thereby releasing guaifenesin at a controlled rate.

Additionally, when at least one additional drug ingredient is present in the combination of hydrophilic and water-insoluble polymers of the sustained release formulation of the present invention, the additional drug ingredient diffuses from the gel when the combination gels when exposed to media of low pH. As discussed above, when the gelled polymer combination is exposed to media of a higher pH, the gel begins to slowly dissolve thereby releasing at least one additional drug ingredient at a controlled rate in addition to the guaifenesin. When using drug ingredients approved by the Food and Drug Administration (FDA), the sustained release formulation may be formulated to mimic the blood serum profile of the additional drug as described in the clinical documents filed with the FDA or as required by the FDA. In other words, the sustained release formulation releases at least one additional drug at a similar rate to the commercially available formulation, thereby providing a therapeutically effective amount of the additional drug.

In a preferred embodiment of the present invention, a sustained release formulation comprises a hydrophilic polymer and a water-insoluble polymer in a ratio of about one-to-one (1:1) to about nine-to-one (9:1), more preferably the range is about three-to-two (3:2) to about six-to-one (6:1), and most preferably the range of hydrophilic polymer to water-insoluble polymer is about two-to-one (2:1) to about four-to-one (4:1). In another embodiment, the sustained release formulation comprises not more than about 10% hydrophilic polymer, preferably, not more than 6%, and in a more preferred embodiment, the sustained release formulation comprises not more than 2.5% of the hydrophilic polymer by weight. In another preferred embodiment, the hydrophilic polymer is hydroxypropyl methylcellulose and the water-insoluble polymer is acrylic resin. The inventors have discovered that the ratios result in a serum concentration profile of guaifenesin that provides an optimal therapeutic concentration for at least twelve hours.

A sustained release formulation of the present invention may be manufactured according to any appropriate method known to those of skill in the art of pharmaceutical manufacture. In one embodiment, guaifenesin and a hydrophilic polymer may be mixed in a mixer with an aliquot of water to form a wet granulation. The granulation may be dried to obtain hydrophilic polymer encapsulated granules of guaifenesin. The resulting granulation may be milled, screened, then blended with various pharmaceutical additives, water insoluble polymer, and additional hydrophilic polymer. The formulation may then tableted and may further be film coated with a protective coating which rapidly dissolves or disperses in gastric juices.

A preferred embodiment of a method of preparing a sustained release formulation of the present invention may comprise loading approximately 126 kg of GUAIFENESIN and about 2 kg of METHOCEL E10M into a high shear mixer. The METHOCEL E10M and GUAIFENESIN may be mixed for about seven minutes at a mixing speed of about 150 RPM and a chopper speed of about 2000 RPM. The mixing and chopping speeds may then be increased to about 200 RPM and 3000 RPM respectively for about five minutes while about 49 kg of water are added to the mixer contents. The mixer may be run for two additional minutes to complete granulation. In a further preferred embodiment, the shut off for the mixer load is set to 21 kilowatts.

The wet granulation may be emptied into a fluid bed bowl and placed into a fluid bed dryer set to a dryer air flow of 900 CFM and an inlet temperature of about 50° C. to about 55° C. until the outlet temperature increases at a rate of 10 per minute. The air flow may then be decreased to 600 CFM, and the inlet temperature may be decreased to 43° C. until the granulation is dried to a moisture content of no more than 0.5%. In another preferred embodiment, the outlet temperature is set to a cut-off of 48° C. In yet another preferred embodiment, an agitator in the fluid bed bowl may be run intermittently during drying. The dried granulation may be passed through a mill fitted with a suitable screen size so that not more than about 30% of the resulting granulation comes through a 100 mesh screen and not more than about 10% of the resulting granulation is retained on a 10 mesh screen. In one preferred embodiment, the dried granulation may be passed through a mill fitted with a 0.109" size screen at a mill speed of about 500 to about 1500 RPM and a screw feed rate of about 35 to about 45 RPM. The resulting screened granulation is about 95% GUAIFENESIN and is called GUAIFENESIN DC (Direct Compressed) herein after. Screened granulation may be transferred to a 10 cubic foot V blender, combined with about another 0.6 kg of METHOCEL E10M, about 0.3 kg of a colorant such as Emerald Green Lake or FD&C BLUE #1, about 0.7 kg of magnesium stearate, and about 1.3 kg of CARBOPOL 974P. The combination may be blended for about three minutes.

In another preferred embodiment of a method of preparing a sustained release formulation of the present invention may comprise loading about 101 kg to about 150 kg of GUAIFENESIN, about 4.5 kg to about 18 kg of the additional drug ingredient, about 4.5 kg to about 5 kg of METHOCEL E10M, about 1.5 kg to about 2.25 kg of CARBOPOL® 974P, and about 40 g to about 240 g of colorant into a high shear mixer. If at this time water is to be added, then about 1 kg to about 1.5 kg of magnesium stearate is added as well. The ingredients may be mixed for about ten to about 12 minutes at a mixing speed of about 150 RPM and a chopper speed of about 2000 RPM. The mixing and chopping speeds may then be increased to about 200 RPM and 3000 RPM, respectively, for about five minutes while optionally about 29 kg of water are added to the mixer contents. If no water is added, then from about 1 kg to about 1.5 kg of magnesium stearate can be added at this time. The mixer may be run for ten additional minutes to complete granulation. In a further preferred embodiment, the shut off for the mixer load is set to 21 kilowatts.

The wet granulation may be emptied into a fluid bed bowl and placed into a fluid bed dryer set to a dryer air flow of 900 CFM and an inlet temperature of about 38° C. to about 48° C. until the outlet temperature increases at a rate of 1° C. per minute. The air flow may then be decreased to 600 CFM, and the inlet temperature may be decreased to 43° C. until the granulation is dried to a moisture content of no more than 0.5%. In another preferred embodiment, the outlet temperature is set to a cut-off of 48° C. In yet another preferred embodiment, an agitator in the fluid bed bowl may be run intermittently during drying. The dried granulation may be passed through a mill fitted with a suitable screen size so that not more than about 30% of the resulting granulation comes through a 100 mesh screen and not more than about 10% of the resulting granulation is retained on a 10 mesh screen. In one preferred embodiment, the dried granulation may be passed through a mill fitted with a size screen of about 0.109" to about 0.125" at a mill speed of about 500 to about 1500 RPM and a screw feed rate of about 35 to about 45 RPM.

The resulting formulations may further be compressed on a tablet compressor machine using tooling to form tablets. The tablets may be any appropriate weight, size, and shape depending on the desired dosage strength of tablet. In one embodiment, these tablets may further be loaded into a coating pan and film coated with Opadry Y-S-3-714 (supplied by Colorcon, Inc.) and air dried in the pan.

Another embodiment of the method of preparing a sustained release formulation of the present invention may comprise blending the drug ingredients, hydrophilic polymer, water insoluble polymer, and any pharmaceutical additives. The resulting blend may then be compressed into tablets and, if desired, film coated with a protective coating which rapidly dissolves or disperses in gastric juices. In a preferred embodiment of such a method, about 126 kg of GUAIFENESIN DC (about 95% purity), about 2.6 kg of METHOCEL E10M, about 1.3 kg of CARBOPOL 974P and about 0.333 kg of a colorant such as Emerald Green Lake or FD&C BLUE #1 may be loaded into a 10 cubic foot V Blender. The ingredients may be blended for about 20 minutes at which time about 0.6 kg of magnesium stearate may be added to the blended ingredients. This mixture may be blended for about another 10 minutes. The resulting formulation may further be compressed on a tablet compressor machine using tooling to form tablets. The tablets may be any appropriate weight, size, and shape depending on the desired dosage strength of the tablet. These tablets may further be loaded into a coating pan and film coated with Opadry Y-S-3-714 (supplied by Colorcon, Inc.) and air dried in the pan.

Figure 4:
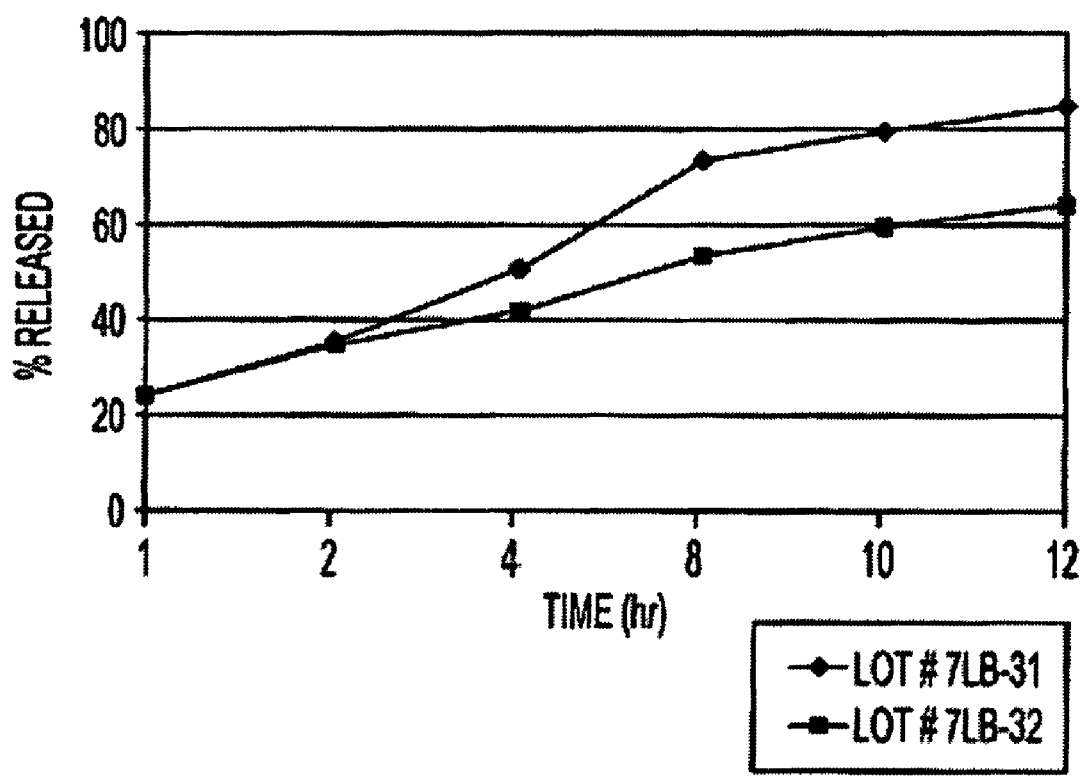
FIG. 4 is a graph demonstrating the dissolution profiles of tablets comprising two different sustained release formulations of the present invention.

Tablets comprising a sustained release formulation of the present invention were prepared and tested for both in vitro and in vivo release characteristics as described in Examples 1, 2, and 3 below. In the in vitro testing, the dissolution rates of these tablets were compared against modified release tablets formulated without acrylic resin (Example 1), and three commercially available tablets, one being an immediate release formulation and the other two being modified release formulations. Tablets comprising the sustained release formulation of the present invention demonstrated a slower, more controlled release of guaifenesin over a twelve hour period than any of the other tablets (see Example 1 and 2, and FIGS. 4 and 5).

Figure 6:
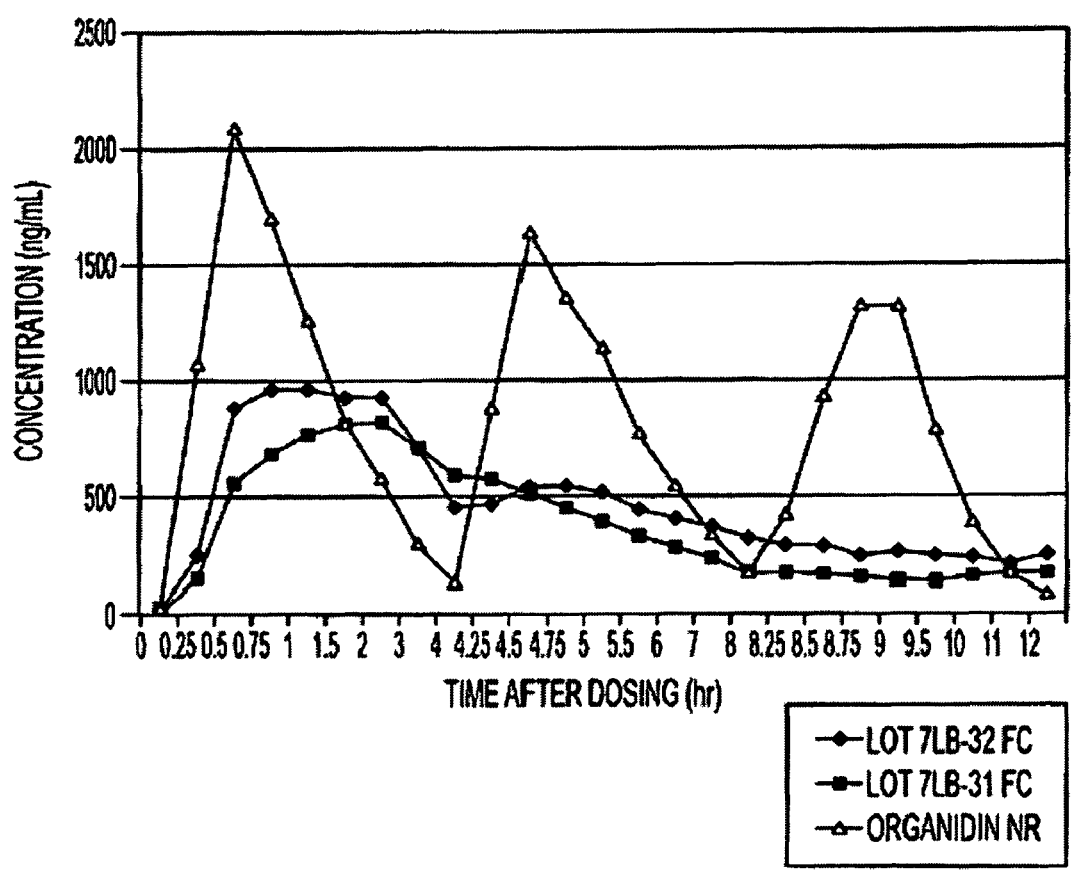
FIG. 6 is a graph demonstrating the plasma concentration of guaifenesin over time in healthy human volunteers who were dosed with three different guaifenesin formulations; an immediate release formulation known in the art, and two different sustained release formulations of the present invention.

In the in vivo testing, serum concentrations of subjects taking tablets comprising the sustained release formulation of the present invention were compared with serum concentrations of subjects taking immediate release guaifenesin tablets and modified release guaifenesin tablets formulated without acrylic resin (see Example 3 and FIG. 6). Tablets comprising the sustained release formulation of the present invention demonstrated improved sustained release and therapeutic concentration at extended time periods that the other two formulations. However, in the subjects taking tablets comprising the sustained release formulation of the present invention, it took longer for guaifenesin to appear in the blood stream and the maximum serum concentration ($C_{max}$) of guaifenesin in these subject was less than half of that of the subjects taking the immediate release tablets.

2. Modified Release Product

To improve the $C_{max}$ and speed of appearance of guaifenesin in patients while maintaining therapeutic effect for at least twelve hours, a portion of a sustained release formulation of the present invention as described above may be combined with a portion of an immediate release formulation in a modified release product. In a preferred embodiment, at least one additional drug ingredient can be present within the sustained release formulation, the immediate release formulation, or both depending upon the desired effect. When using drug ingredients approved by the Food and Drug Administration (FDA), the sustained release formulation, immediate release formulation, or both may be formulated to mimic the blood serum profile of the additional drug as described in the clinical documents filed with the FDA or as required by the FDA. In other words, the sustained and/or immediate release formulations of the modified release product may release the at least one additional drug at a similar rate to the commercially available formulation, thereby providing a therapeutically effective amount of the additional drug.

The modified release product can be in the form of bi-layered tablets, capsules having a combination of beads or granules of immediate release formulation and sustained release formulation, or a tablet wherein the sustained release formulation comprises a core that is coated by a layer of the immediate release formulation. For purpose of illustration only, the invention will be described in detail in the context of the bi-layered tablet embodiment.

The immediate release formulation may comprise guaifenesin and various pharmaceutical additives such as lubricants, colorants, binders, glidants, surface active agents, preservatives, stabilizers, as described above and/or any other pharmaceutical additives known to those of skill in the art. In one embodiment, the immediate release layer comprises at least one drug ingredient. In another embodiment, the immediate release layer comprises at least two drug ingredients. In a more preferred embodiment, an immediate release formulation comprises guaifenesin, microcrystalline cellulose, sodium starch glycolate, and magnesium stearate. In another more preferred embodiment, an immediate release formulation comprises guaifenesin, at least one drug ingredient, microcrystalline cellulose, hydroxypropyl methylcellulose, sodium starch glycolate, and magnesium stearate. In yet another preferred embodiment, an immediate release formulation may comprise about 47% to about 58% guaifenesin, about 32% to about 42% microcrystalline cellulose, about 3% to about 8% sodium starch glycolate, and about 0.3% to about 0.5% magnesium stearate by weight. In yet another preferred embodiment, an immediate release formulation may comprise about 47% to about 58% guaifenesin, about 3% to about 5% of at least one additional drug ingredient, about 32% to about 42% microcrystalline cellulose, about 2% to about 5% hydroxypropyl methylcellulose, about 3% to about 8% sodium starch glycolate, and about 0.3% to about 0.5% magnesium stearate by weight.

The bi-layer tablet may be manufactured according to any method known to those of skill in the art. The resulting tablet may comprise the two portions compressed against one another so that the face of each portion is exposed as either the top or bottom of the tablet, or the resulting tablet may comprise the sustained release portion in the center coated by the immediate release portion so that only the immediate release portion is exposed. In a preferred embodiment, a bi-layer tablet of the present invention comprises the two portions compressed against one another so that the face of each portion is exposed.

In a preferred method of manufacturing the bi-layer tablets of the present invention a sustained release formulation is prepared according to either a wet granulation or dry granulation method as described above. The immediate release formulation may be prepared by simply blending the guaifenesin with any pharmaceutical additives. If at least one additional drug ingredient is present, then water may be added to the formulation, as described above. In a further preferred embodiment, appropriate quantities of GUAIFENESIN DC, microcrystalline cellulose, and sodium starch glycolate are blended in a 10 cubic foot blender for about twenty minutes. An appropriate quantity of magnesium stearate is then added to the ingredients and blended for about ten more minutes to make an immediate release formulation. Portions of the sustained release formulation and immediate release formulation are then compressed by a tablet compressor machine capable of forming bi-layer tablets. In one embodiment, these tablets may further be coated with a protective film which rapidly disintegrated or dissolves in gastric juices.

The tablets may be made with any ratio of guaifenesin to at least one additional drug ingredient which results in a blood profile demonstrating appropriate therapeutic effect over extended time periods. As discussed above, the additional drug ingredient may be present in an amount sufficient to mimic the blood serum profile of the commercially available formulation of the drug and not to exceed the maximum dose approved by the FDA for the treatment, prevention, or amelioration of a particular illness or disease. In one embodiment, the ratio in the sustained release formulation of guaifenesin to at least one additional drug ingredient is about one point one-to-one (1.1:1) to about four-to-one (4:1) by weight, preferably, the ratio is about three-to-two (3:2) to about nine-to-one (9:1) by weight, and more preferably, the ratio of guaifenesin to at least one additional drug ingredient is about three-to-one (3:1) to about 20:1 by weight. When present in the immediate release layer, the amount of the at least one additional drug should be sufficient to match the drug release profile of the additional drug within the sustained release profile. Within this embodiment, the ratio in the immediate release formulation of guaifenesin to at least one additional drug ingredient, if present, is about four-to-one (4:1) to about one-to-one (1:1), preferably, the ratio is about nine-to-one (9:1) to about three-to-two (3:2), and more preferably, the ratio of guaifenesin to at least one additional drug ingredient is about nine-to-one (9:1) to about (12:1) by weight.

The tablets may be made with any ratio of sustained release to immediate release formulation which results in a blood profile demonstrating appropriate therapeutic effect over extended time periods. In one embodiment, the bi-layer tablets comprise guaifenesin distributed within the sustained release formulation and the immediate release formulation wherein the ratio of guaifenesin is about one-to-one (1:1) to about 49:1 by weight, preferably the ratio is about three-to-two (3:2) to about 19:1, and more preferably, the ratio of guaifenesin distributed within the sustained release formulation and the immediate release formulation is about five-to-one (5:1) to about nine-to-one (9:1) by weight, respectively. For example, in a 1200 mg bi-layer modified release guaifenesin tablet of the present invention, there may be about 200 mg of guaifenesin in the immediate release layer and about 1000 mg of guaifenesin in the sustained release layer.

The tablets may be made with at least one additional drug only within the sustained release formulation. Optionally, however, the tablets may be made with at least one additional drug distributed within the sustained release formulation and the immediate release formulation. In one embodiment, the bi-layer tablets comprise a additional drug ingredient distributed within the sustained release formulation and immediate release formulation wherein the ratio of additional drug ingredient is about one-to-one (1:1) to about 19:1 by weight, preferably the ratio is about three-to-two (3:2) to about nine-to-one (9:1), and more preferably the ratio of additional drug ingredient distributed within the sustained release formulation and the immediate release formulation is about three-to-one (3:1) to about four-to-one (4:1) by weight, respectively.

In one preferred embodiment of manufacturing a 1200 mg bi-layer sustained release guaifenesin tablet, about 105 kg of GUAIFENESIN DC, about 2.5 kg of METHOCEL E10M, about 1.25 kg of CARBOPOL 974P, and about 0.333 kg of Emerald Green Lake or FD&C BLUE #1 in a 10 cubic foot P.K. blender for about twenty minutes. About 0.6 kg of magnesium stearate may then be added and blending continued for about another ten minutes to prepare the sustained release formulation. Approximately 21 kg of GUAIFENESIN DC, approximately 11.75 kg of microcrystalline cellulose, and approximately 3 kg of sodium starch glycolate may be blended in a 3 cubic foot P.K. blender for about twenty minutes. Approximately 0.1 kg of magnesium stearate may then be added and blending continued for about another ten minutes to prepare the immediate release formulation. The two formulations may then be compressed to make bi-layer tablets wherein about 75% of each tablet may be sustained release formulation and about 25% if each tablet may be immediate release formulation. The tablets may be any dosage strength, size, or shape. In a preferred embodiment, 1200 mg tablets are round and about ⅝ inch in diameter, about 0.28 inch-0.31 inch in thickness, weigh about 1.46 grams and have a hardness range of about 15-40 SCU. In another preferred embodiment, 600 mg tablets are round and about ½ inch in diameter, about 0.218 inch-0.230 inch in thickness, weigh about 0.729 grams and have a hardness range of about 12-30 SCU.

In another preferred embodiment of manufacturing a 1200 mg bi-layer sustained release guaifenesin tablet, about 101 kg of GUAIFENESIN DC, about 4.5 kg of at least one additional drug ingredient such as dextromethorphan, about 5 kg of METHOCEL E10M, about 1.5 kg of CARBOPOL 974P, and about 0.04 kg of FD&C BLUE #1 are blended in a 10 cubic foot Day mixer for about twelve minutes. Thereafter, about 29 kg of water is added and the mixture is blended for an additional 10 minutes, followed by drying. About 1 kg of magnesium stearate may then be added and blending continued for about another ten minutes to prepare the sustained release formulation. About 45.6 kg of GUAIFENESIN, about 3.6 kg of at least one additional drug ingredient such as dextromethorphan, about 40.32 kg of microcrystalline cellulose, and approximately 3 kg of sodium starch glycolate are blended in a 3 cubic foot Day mixer for about 12 minutes. Thereafter, about 36 kg of water is added and the mixture is blended for an additional 10 minutes, followed by drying. About 0.48 kg of magnesium stearate may then be added and blending continued for about another ten minutes to prepare the immediate release formulation. The two formulations may then be compressed to make bi-layer tablets wherein about 75% of each tablet may be sustained release formulation and about 25% if each tablet may be immediate release formulation. The tablets may be any dosage strength, size, or shape. In a preferred embodiment, 1200 mg tablets are round and about ⅝ inch in diameter, about 0.31 inch-0.34 inch in thickness, weigh about 15.3 grams and have a hardness range of about 15-35 SCU. In another preferred embodiment, 600 mg tablets are round and about ½ inch in diameter, about 0.22 inch-0.26 inch in thickness, weigh about 7.65 grams and have a hardness range of about 15-65 SCU.

The immediate release portion of the bi-layer tablet is formulated to dissolve in aqueous media of low pH, such as that found in the stomach, to quickly release the guaifenesin contained within the portion. This results in rapid bioavailability of a high concentration of guaifenesin. As demonstrated in Example 6 and FIGS. 9 and 10 below, the immediate release portion of the bi-layer tablet results in a maximum serum concentration ($C_{max}$) and time of maximum serum concentration ($T_{max}$) equivalent to the $C_{max}$ obtained when the first of three doses of a standard immediate release formulation having one third the amount of guaifenesin is dosed every four hours over a 12 hour period.

The sustained release portion gels when exposed to media of low pH allowing the sustained release portion of the tablet to be passed into the intestinal tract. In the intestines, the gelled sustained release portion is exposed to media of a higher pH, causing the gel to slowly dissolve, thereby allowing guaifenesin to diffuse and dissolve out of the gelled matrix. This results in controlled bioavailability over an extended time period (i.e. twelve or more hours) causing the tablet to provide extended therapeutic effect. This result is evidenced in Example 6 and FIGS. 9 and 10 below—the half-life of the modified release bi-layer tablet is increased to more than 3 hours and the tablet has an $AUC_{inf}$ (the area under a plasma concentration versus time curve from time 0 to infinity) of greater than 8000 hr*ng/mL. As demonstrated in Example 7 and FIG. 11, the bi-layer tablets of the present invention had a further surprising result in that a 600 mg tablet had a $T_{max}$ equivalent to that of a 1200 mg and a $C_{max}$ and $AUC_{inf}$ approximately half of a 1200 mg tablet. Thus, without adjusting or changing the composition of the sustained release formulation or bi-layer tablet, a lower dosage strength guaifenesin tablet of the present invention exhibits plasma concentration profile that is approximately directly proportional to that of a higher dosage strength guaifenesin tablet also of the present invention. As further demonstrated in Example 7 and FIG. 11, the bi-layer tablets of the present invention had another surprising result in that the $C_{max}$ and $AUC_{inf}$ of a 1200 mg tablet administered to volunteers who had been fasting and the $C_{max}$ and $AUC_{inf}$ of a 1200 mg tablet administered to volunteers who had consumed a high fat meal were approximately equivalent. Thus, a bi-layer tablet of the present invention demonstrates a reduced food effect, being approximately equally effective when administered to a patient on an empty or full stomach.

Three batches of the 1200 mg guaifenesin-60 mg dextromethorphan HBr formulation of Example 8 were dissolved to determine the amount of dextromethorphan HBr released over time. Generally, the formulations had 1200 mg of guaifenesin and 60 mg dextromethorphan HBr and were studied over a 12 hour period. The released amount of dextromethorphan HBr was determined as a weight percent of dissolved dextromethorphan in contrast to the total weight of dextromethorphan prior to dissolution. After 1 hour about 46% to 47% of the dextromethorphan had dissolved. After 2 hours the about 59% to 60% had dissolved, after 6 hours 73% to 76% had dissolved, and after 12 hours about 86% to 89% by weight of the dextromethorphan had dissolved. Thus, the formulations of the invention reproducibly release dextromethorphan over time. See FIG. 12.

A reference sustained release formulation of guaifenesin was compared to two formulations of the present invention. Formulations B and C of FIG. 13, exhibited guaifenesin release profiles similar to the reference formulation. The reference formulation for FIG. 13 was formulation IV of Example 5. Formulation B comprised 77% guaifenesin by weight, 3.8% by weight dextromethorphan, 9.1% by weight microcrystalline cellulose, 1.9% by weight METHOCEL E10M, and 0.9% CARBOPOL® 974P. Formulation C comprised 76.5% by weight guaifenesin, 3.8% by weight dextromethorphan, 9.7% by weight microcrystalline cellulose, 1.9% by weight METHOCEL E10M, and 0.9% by weight CARBOPOL® 974P. Formulations B and C exhibited similar behavior and had a guaifenesin release profile similar to the reference formulation. Accordingly, the combination formulations of the invention did not interfere with the release of guaifenesin. In particular, after 12 hours Formulation C released a greater dose of guaifenesin than the reference formulation.

Figure 13:
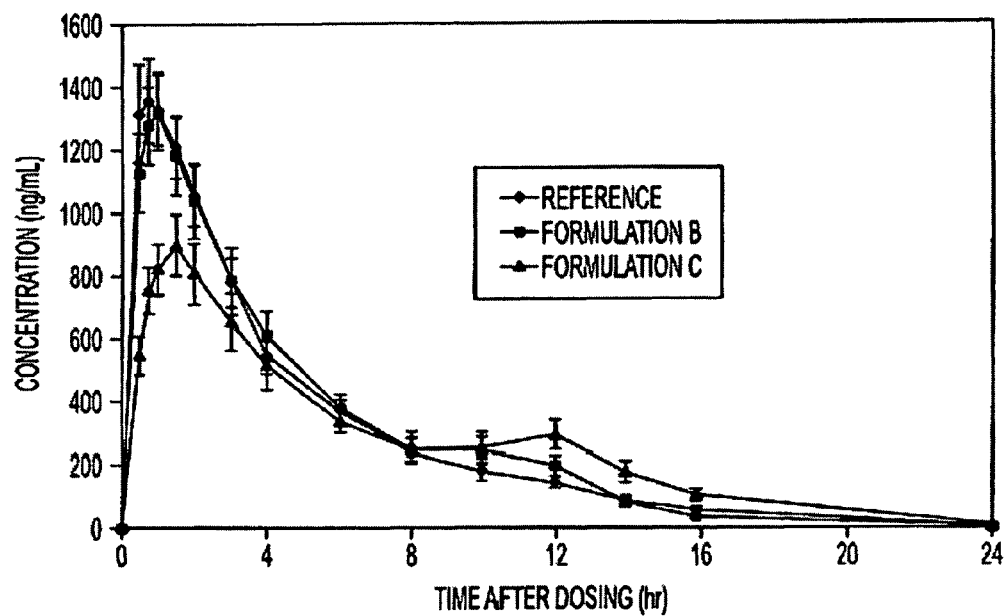
FIG. 13 is a graph demonstrating the plasma concentration of guaifenesin following the administration of 1200 mg guaifenesin and 60 mg dextromethorphan HBr to volunteers separately and in formulations of the present invention.
Figure 14:
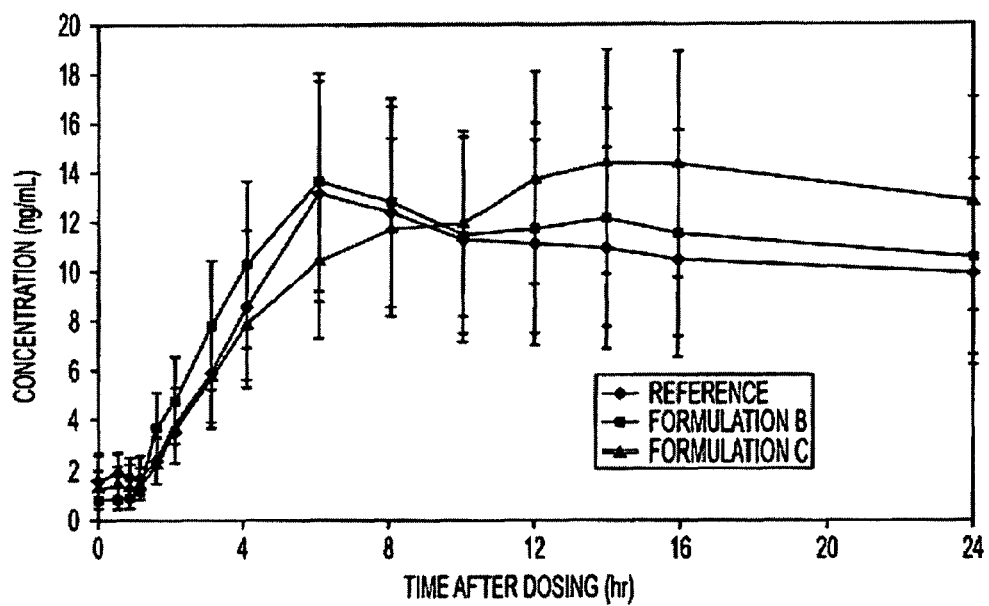
FIG. 14 is a graph demonstrating the plasma concentrations of dextromethorphan HBr following the administration of 1200 mg guaifenesin and 60 mg dextromethorphan HBr to volunteers in three different formulations.

Formulations B and C of FIG. 13 were compared against a reference consisting of an extended release formulation of dextromethorphan commercially available under the name Delsym sold by Celltech Medica. The comparison was carried out to determine the behavior of guaifenesin-dextromethorphan formulations of the invention as compared to separately administered combination formulations of dextromethorphan. Formulations B and C had longer dextromethorphan release profiles than the reference, as shown in FIG. 14. Additionally, the combined formulations of the present inventions had no detrimental effect upon the release profile of dextrorphan.

Figure 15:
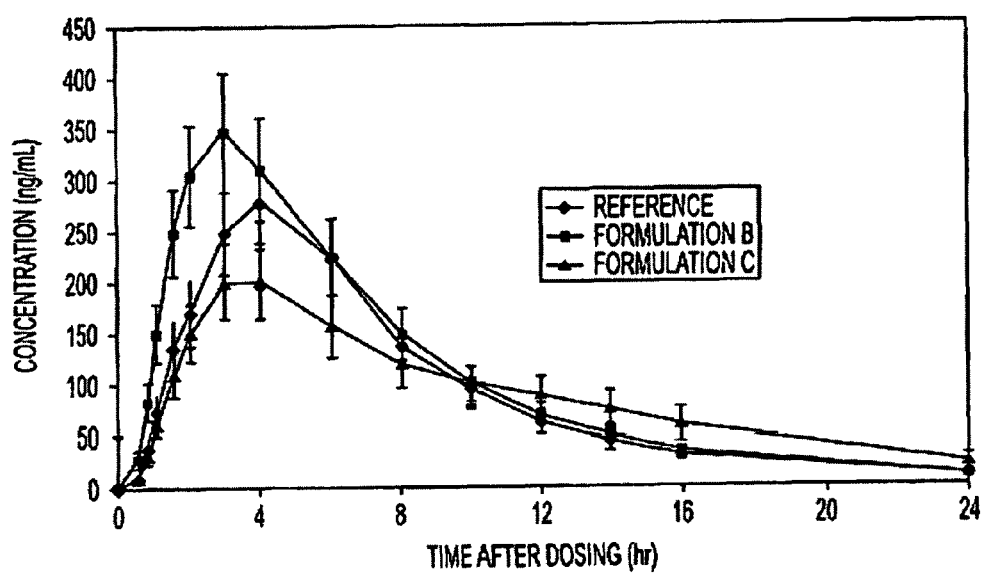
FIG. 15 is a graph demonstrating the plasma concentrations of the metabolite dextrorphan following the administration of 1200 mg guaifenesin and 60 mg dextromethorphan HBr to volunteers in three different formulations.

Another method to monitor dextromethorphan plasma concentrations is to measure the plasma concentration of the metabolite dextrorphan. The plasma concentration of dextrorphan metabolite of the reference formulation and Formulations B and C of FIG. 14 were plotted in FIG. 15. Generally, the formulations exhibited similar dextrorphan concentrations, with Formula C exhibiting the highest dextrorphan concentration after 12 hours. FIG. 15 demonstrates that the formulations of the present invention containing guaifenesin do not inhibit the release of dextromethorphan, as determined by measuring the presence of the metabolite dextrorphan.

Three batches of the 1200 mg guaifenesin-120 mg pseudoephedrine HCl formulation of Example 10 were dissolved to determine the amount of pseudoephedrine HCl released over time. Generally, the formulations had 1200 mg of guaifenesin and 120 mg pseudoephedrine HCl and were studied over a 12 hour period. The released amount of pseudoephedrine HCl was determined as a weight percent of dissolved pseudoephedrine HCl in contrast to the total weight of pseudoephedrine HCl prior to dissolution. After 1 hour about 43% to 45% of the pseudoephedrine HCl had dissolved. After 2 hours the about 58% to 60% dissolved, after 6 hours 82% to 89% had dissolved, and after 12 hours about 96% to 97% by weight of the pseudoephedrine HCl had dissolved. See FIG. 16.

Figure 17:
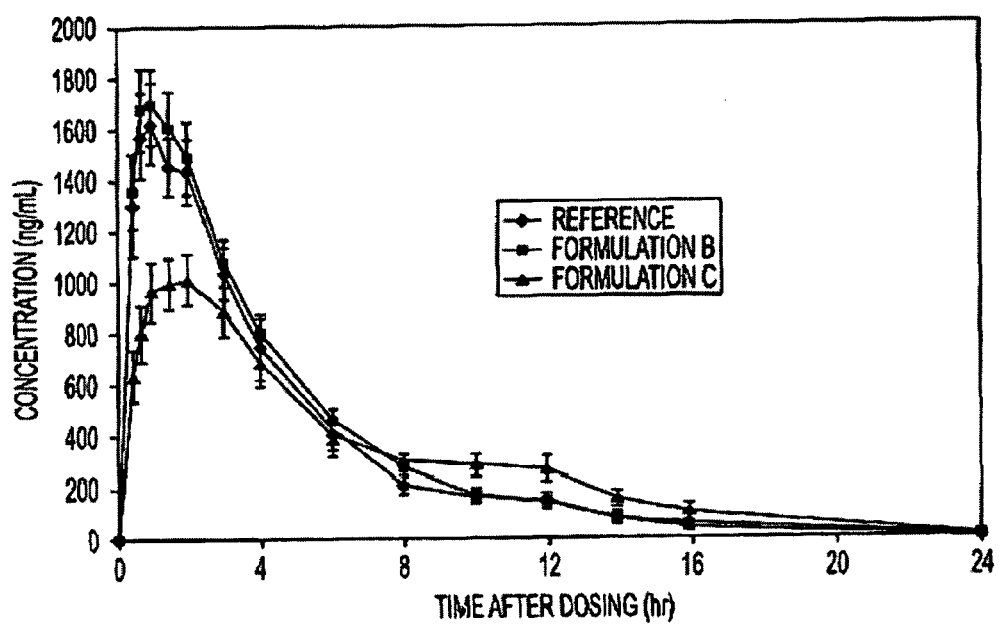
FIG. 17 is a graph demonstrating the plasma concentration of guaifenesin following the administration of 1200 mg guaifenesin and 120 mg pseudoephedrine HCl to volunteers separately and in formulations of the present invention.

Three formulations of guiafenesin, two also containing an additional ingredient, pseudoephedrine, were compared to determine whether an additional ingredient affects the release profile of guiafenesin. In FIG. 17, the reference formulation included formulation IV of Example 5 and a separate Sudafed® 12 hour formulation available from Pfizer Inc. 201 Tabor Road, Morris Plains, N.J., 07950. The reference formulation was compared to Formulation B and Formulation C of the present invention. Formulation B comprised a sustained release formulation having 86% by weight guaifenesin DC, 9.8% by weight pseudoephedrine HCl, 2.4% by weight hydroxypropyl methylcellulose, and 1.2% by weight CARBOPOL® 974P, and an immediate release formulation having 52% by weight guaifenesin DC and 39% by weight microcrystalline cellulose by weight. Formulation C comprised 77% by weight guaifenesin DC, 7.7% by weight pseudoephedrine, 9% by weight microcrystalline cellulose, 1.8% by weight METHOCEL E10M, and 0.9% by weight CARBOPOL® 974P. Formulations B and C exhibited similar behavior to separately administered formulations, thus demonstrating that formulations of the present invention did not interfere with the profile release of pseudoephedrine.

Figure 18:
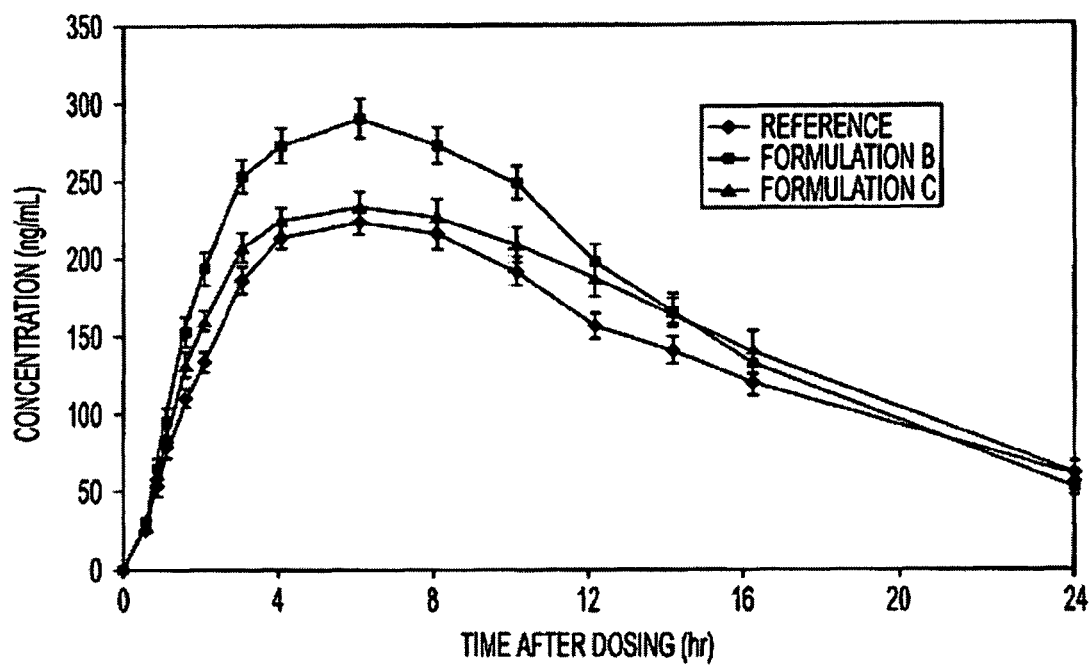
FIG. 18 is a graph demonstrating the plasma concentration of pseudoephedrine HCl following the administration of 1200 mg guaifenesin and 120 mg pseudoephedrine HCl to volunteers in three different formulations.

The plasma concentration for pseudoephedrine HCl was studied to determine whether the formulations of the present invention interfered with the release profile of pseudoephedrine. The pseudoephedrine plasma concentrations for the formulations of FIG. 17 were plotted over a 24 hour period. As illustrated in FIG. 18, Formulations B and C of FIG. 17 exhibited higher pseudoephedrine concentrations than the reference formulation. Thus, the combined formulations of the present invention release pseudoephedrine in comparable or better release profiles than formulations containing pseudoephedrine alone.

EXAMPLES

The invention is further defined by reference to the following examples describing in detail the preparation of the composition and methods of the present invention, as well as their utility. It will be apparent to those skilled in the art that many modifications, both to materials and methods, may be practiced without departing from the purpose and interest of this invention.

Example 1

A batch of sustained release guaifenesin tablets, Lot# 7LB-31FC, with the following composition was prepared:

| Components | Weight per Tablet |
|---|---|
| GUAIFENESIN DC | 1260 mg |
| METHOCEL E10M | 30 mg |
| Emerald Green Lake | 4 mg |
| Magnesium Stearate | 6.8 mg |
| Opadry Y-S-3-7413 | 13.01 mg |

Another batch of sustained release guaifenesin tablets, Lot# 7LB-32FC, with the following composition was prepared:

| Components | Weight per Tablet |
|---|---|
| GUAIFENESIN DC | 1260 mg |
| METHOCEL E10M | 30 mg |
| CARBOPOL 974P | 15 mg |
| Emerald Green Lake | 4 mg |
| Magnesium Stearate | 6.8 mg |
| Opadry Y-S-3-7413 | 13.16 mg |

Six tablets from Lot 7LB-31FC and six tablets from Lot 7LB-32FC were tested for in vitro guaifenesin release using an Acid/Base dissolution (slightly modified USP 23/NF 18 <711> Drug Release using Apparatus 2). Six dissolution vessels of a USP calibrated Hanson dissolution bath, equipped with shafts and paddles, were filled with 675 ml of 0.1N hydrochorlic acid at 37.0° C. The bath and vessels were maintained at a temperature of 37.0±0.5° C. throughout the 12 hr. dissolution test. The paddles were set to rotate at 50 RPM and slowly lowered into the vessels. One tablet of lot 7LB-31 was then dropped into each vessel.

A the one hour and two hour intervals of testing, 5 ml samples of dissolution solution were withdrawn from each vessel and filtered through a 10 micron polyethylene filter into glass HPLC vials. Immediately after the two hour samples were withdrawn, 225 ml of 0.2M sodium phosphate tribasic was added to each vessel to increase the solution pH to about 6.8. The dissolution was run for ten more hours, 2.0 ml samples being withdrawn from each vessel at the 4 hr., 8 hr., 10 hr., and 12 hr. intervals. The filtered samples from each sampling interval were then run on an HPLC to determine percent guaifenesin released from each tablet at each of the sampling intervals.

The same dissolution testing procedure was performed for lot 7LB-32 FC. The lots gave dissolution profiles shown below and depicted in FIG. 4.

Lot 7LB-31

| Vessel # | 1 HR | 2 HR | 4 HR | 8 HR | 10 HR | 12 HR |
|---|---|---|---|---|---|---|
| 1 | 26 | 38 | 55 | 77 | 84 | 88 |
| 2 | 27 | 39 | 54 | 75 | 81 | 86 |
| 3 | 22 | 37 | 50 | 73 | 78 | 85 |
| 4 | 23 | 33 | 47 | 64 | 73 | 79 |
| 5 | 25 | 36 | 52 | 75 | 81 | 86 |
| 6 | 24 | 35 | 49 | 74 | 81 | 87 |
| Average | 24.5 | 36.3 | 51.2 | 73.0 | 79.7 | 85.2 |

Lot 7LB-32FC

| Vessel # | 1 HR | 2 HR | 4 HR | 8 HR | 10 HR | 12 HR |
|---|---|---|---|---|---|---|
| 1 | 25 | 36 | 42 | 54 | 59 | 64.0 |
| 2 | 24 | 35 | 42 | 55 | 61 | 66 |
| 3 | 26 | 38 | 45 | 59 | 65 | 69 |
| 4 | 24 | 35 | 42 | 54 | 60 | 65 |
| 5 | 24 | 36 | 43 | 54 | 59 | 64 |
| 6 | 23 | 34 | 38 | 50 | 55 | 59 |
| Average | 24.3 | 35.7 | 42.0 | 54.3 | 59.8 | 64.5 |

Both formulations demonstrated sustained release of guaifenesin over a 12 hour period. Lot 7LB-32FC demonstrated identical release properties to Lot 7LB-31FC in 0.1N HCl. In buffered solution, however, Lot 7LB-32FC, the lot comprising a 2:1 ratio of METHOCEL E10M to CARBOPOL 974P, demonstrated a statistically slower release than Lot 7LB-31FC, comprising METHOCEL E10M and no CARBOPOL 974P. A slower release rate in vitro translates to a slower, more controlled release with longer drug action in vivo—a favorable characteristic for pharmaceutical products containing a high concentration of an active ingredient with a short half-life.

Example 2

Figure 5:
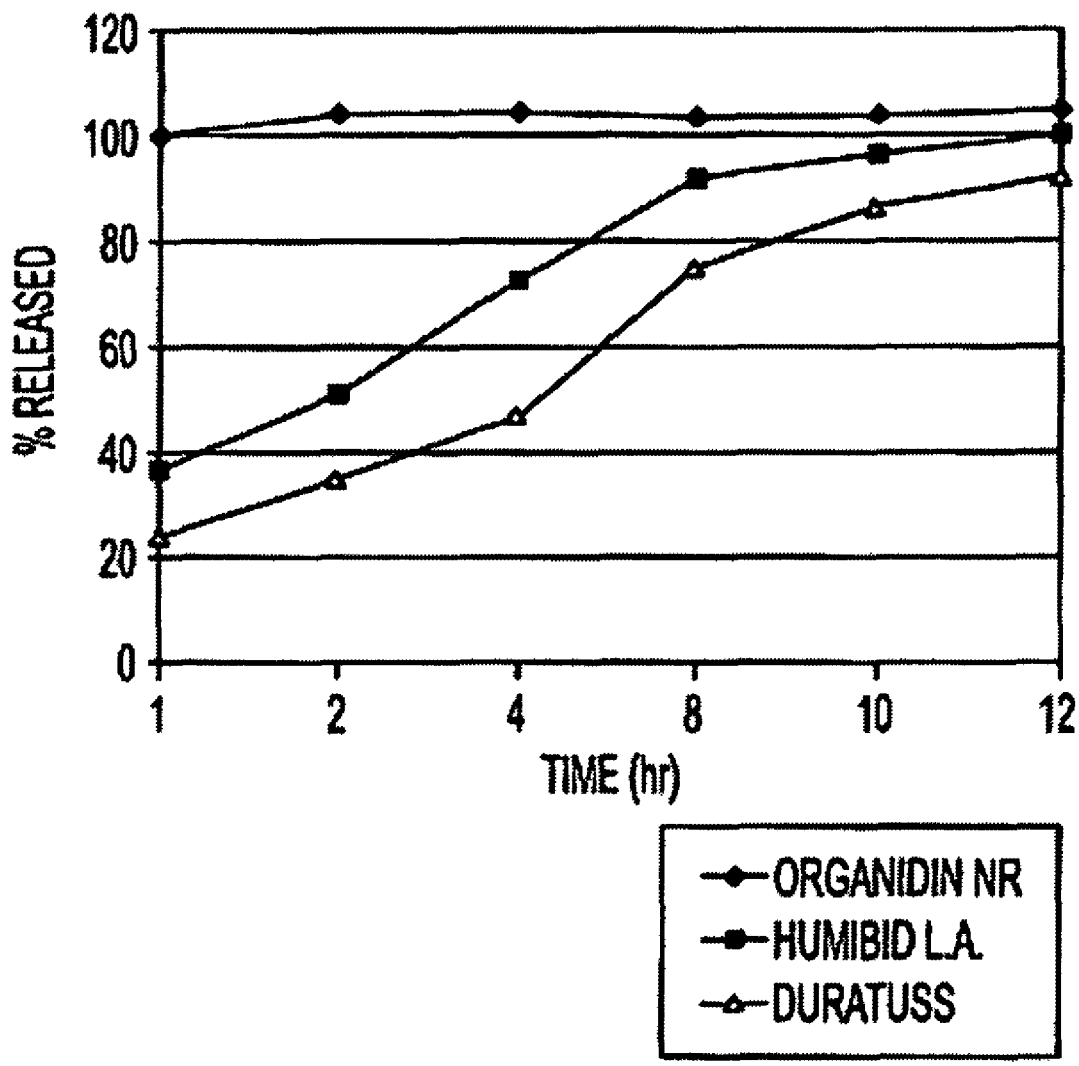
FIG. 5 is a graph demonstrating the dissolution profiles of an immediate release dosage form and two sustained release dosage forms of guaifenesin, all of which are known in the art.

A dissolution study was run to compare dissolution profiles of lots 7LB-32FC and 7LB-31FC with currently available guaifenesin dosage forms. One immediate release tablet, ORGANIDIN NR, and two sustained release tablets, HUMIBID L.A. and DURATUSS, were subjected to the same dissolution study as described for lots 7LB031FC and 7LB-32FC in Example 1 above. The following is a summary of the results which are also depicted in FIG. 5.

| | ORGANIDIN NR % guaifenesin released | HUMIBID L.A. % guaifenesin released | DURATUSS % guaifenesin released |
|---|---|---|---|
| 1 Hr | 100 | 36 | 24 |
| 2 Hr | 103 | 51 | 35 |
| 4 HR | 104 | 72 | 47 |
| 8 HR | 103 | 91 | 75 |
| 10 HR | 103 | 96 | 86 |
| 12 HR | 105 | 100 | 92 |

The immediate release ORGANIDIN released 100% of guaifenesin content within the first hour of dissolution. The two sustained release dosage forms which are currently available both demonstrated a slower release of guaifenesin. However, both the HUMIBID LA and DURATUSS released guaifenesin more rapidly than either Lot 7LB-31FC or 7LB-32FC. Both HUMIBID LA and DURATUSS would, therefore, exhibit a faster rate of release and thus a shorter lived therapeutic effect in vivo.

Example 3

The in vivo behavior of sustained release tablets of Lot 7LB-31FC and Lot 7LB-32FC from Example 1 were compared to the in vivo behavior of an immediate release formulation (ORGANIDIN NR). The open-label study involved 9 healthy volunteers averaging 38±11.01 years of age with a range of 23 years to 55 years of age. The subjects weighed 175.56±24.22 lbs. with a range of 143 to 210 lbs. One subject was female and the remainder were male. Each subject received either one 1200 mg dose of one of the two above described sustained release tablets or 400 mg every four hours for 3 doses of the immediate release formulation.

Blood samples (7 ml with sodium heparin as anticoagulant) were taken prior to dosing and at specific intervals up to 12 hours after dosing. All blood samples were chilled and centrifuged within 30 minutes of being drawn. The plasma was separated, transferred to a polypropylene tube, frozen at −20° C. or below and stored frozen until being shipped for guaifenesin analysis.

The plasma samples were analyzed by a fully validated HPLC method. The results are depicted in FIG. 6. This resulting plasma concentration v. time data was subjected to pharmacokinetic analysis using non-compartmental analysis with Winnonlin 1.5. The results of the pharmacokinetic parameters analysis are below.

| Subject | Formulation | $T_{max}$ (hr.) | $C_{max}$ (ng/ml) | $AUC_{0-12}$ (hr * ng/ml) | $T_{1/2}$ (hrs.) | $AUC_{inf}$ (hr * ng/ml) |
|---|---|---|---|---|---|---|
| 1 | 7LB-31FC | 2.00 | 827.02 | 4817.20 | 4.64 | 6339.25 |
| 2 | 7LB-31FC | 1.50 | 834.65 | 4695.89 | 2.71 | 5291.71 |
| 3 | 7LB-31FC | 1.50 | 802.44 | 4142.14 | 3.44 | 4728.33 |
| 4 | 7LB-32FC | 0.75 | 625.48 | 3034.31 | 5.78 | 5134.35 |
| 5 | 7LB-32FC | 1.00 | 1052.00 | 5872.46 | 5.99 | 8298.33 |
| 6 | 7LB-32FC | 2.00 | 1372.00 | 7924.35 | 5.53 | 9557.78 |
| 7 | ORGANIDIN NR | 0.50 | 2140.00 | 6921.94 | 0.86 | 7009.68 |
| 8 | ORGANIDIN NR | 4.25 | 18.17.00 | 6598.26 | 0.73 | 6674.65 |
| 9 | ORGANIDIN NR | 0.50 | 2831.00 | 9389.76 | 0.81 | 9570.91 |
| Mean | 7LB-31FC | 1.67 | 821.37 | 4551.74 | 3.59 | 5453.10 |
| Mean | 7LB-32FC | 1.25 | 1016.49 | 5610.37 | 5.77 | 7663.49 |
| Mean | ORGANIDIN NR | 1.75 | 2262.67 | 7636.65 | 0.80 | 7751.74 |
| Ratio (%) | 7LB-31FC/IR | 95.24 | 36.30 | 59.60 | 448.27 | 70.35 |
| Ratio (%) | 7LB-32FC/IR | 71.43 | 44.92 | 73.47 | 718.92 | 98.86 |

Subjects given the 1200 mg formulation 7LB-32FC reached maximum plasma guaifenesin concentrations of 1016 ng/mL in 1.25 hours and had an $AUC_{inf}$ of 7663 hr*ng/ml. The subjects given formulation 7LB-31FC reached maximum plasma guaifenesin concentrations of 821 ng/mL in 1.67 hours and had an $AUC_{inf}$ of 5453 hr*ng/ml. The subjects given the immediate release formulation, ORGANIDIN NR, reached maximum plasma guaifenesin concentrations of 2263 ng/ml in 1.75 hours (2 subjects peaked at 0.5 hours after the first dose and the third peaked at 0.25 hours after the second dose at 4 hours) and had an $AUC_{inf}$ of 7752 hr*ng/ml. The two controlled release formulations demonstrated sustained release in that their half-lives were longer, 5.77 hours for the 7LB-32FC and 3.59 hours for the 7LB-31FC compared to 0.8 hours for the immediate release formulation, ORGANIDIN NR.

Both formulations 7LB-32FC (with both METHOCEL E10M and CARBOPOL 974P) and 7LB-31FC (with METHOCEL E10M only) control the release of guaifenesin from the tablet compared to the immediate release ORGANIDIN NR. Formulation 7LB-32FC, the formulation containing a 6:1 ratio of METHOCEL E10M to CARBOPOL 974P, had the longest half life at 5.77 hours with the largest $AUC_{inf}$ between the two sustained release formulation. However, both sustained release formulation has a $C_{max}$ that was less than half of the $C_{max}$ of the immediate release ORGANIDIN NR.

Example 4

Three different modified release tablet lots were prepared with the following compositions:

Sustained Release Formulation I, non-layered tablet

| Components | Weight per Tablet |
|---|---|
| GUAIFENESIN DC | 1260 mg |
| METHOCEL E10M | 40 mg |
| CARBOPOL 974P | 20 mg |
| Emerald Green Lake | 4 mg |
| Magnesium Stearate | 6.8 mg |

Sustained Release Formulation II, bi-layered, 400 mg IR and 800 mg SR

IR Formulation

| Components | Weight per Tablet |
|---|---|
| GUAIFENESIN DC | 421 mg |
| Microcrystalline Cellulose (AVICEL) | 40 mg |
| Sodium Starch Glycolate (EXPLOTAB) | 60 mg |
| Magnesium Stearate | 2 mg |

SR Formulation

| Components | Weight per Tablet |
|---|---|
| GUAIFENESIN DC | 842 mg |
| METHOCEL E10M | 27 mg |
| CARBOPOL 974P | 13.5 mg |
| Emerald Green Lake | 3 mg |
| Magnesium Stearate | 4.5 mg |

Sustained Release Formulation III, bi-layered, 600 mg IR and 600 mg SR
IR Formulation

| Components | Weight per Tablet |
| --- | --- |
| GUAIFENESIN DC | 630.8 mg |
| Microcrystalline Cellulose (AVICEL) | 353 mg |
| Sodium Starch Glycolate (EXPLOTAB) | 90.1 mg |
| Magnesium Stearate | 3 mg |

SR Formulation

| Components | Weight per Tablet |
| --- | --- |
| GUAIFENESIN DC | 630.8 mg |
| METHOCEL E10M | 40 mg |
| CARBOPOL 974P | 20 mg |
| Emerald Green Lake | 4 mg |
| Magnesium Stearate | 6.8 mg |

The in vivo behavior of each of the three sustained release tablets and an immediate release formulation (ORGANIDIN NR) were compared. The open-label study involved 15 healthy volunteers averaging 31.67±11.89 years of age with a range of 20 years to 51 years of age. The subjects weighed 162.00±25.05 lbs. with a range of 123 to 212 lbs. All 15 subjects were administered 400 mg of the immediate release formulation every 4 hours for a total of 12 hours in on one day. On another day, 5 subjects were administered Sustained Formulation I, another 5 subjects were administered Sustained Formulation II, and yet another 5 subjects were administered Sustained Formulation III.

Blood samples (7 ml with sodium heparin as anticoagulant) were taken prior to dosing and at specific intervals up to 12 hours after dosing. All blood samples were chilled and centrifuged within 30 minutes of being drawn. The plasma was separated, transferred to a polypropylene tube, frozen at −20° C. or below and stored frozen until being shipped for guaifenesin analysis.

Figure 7:
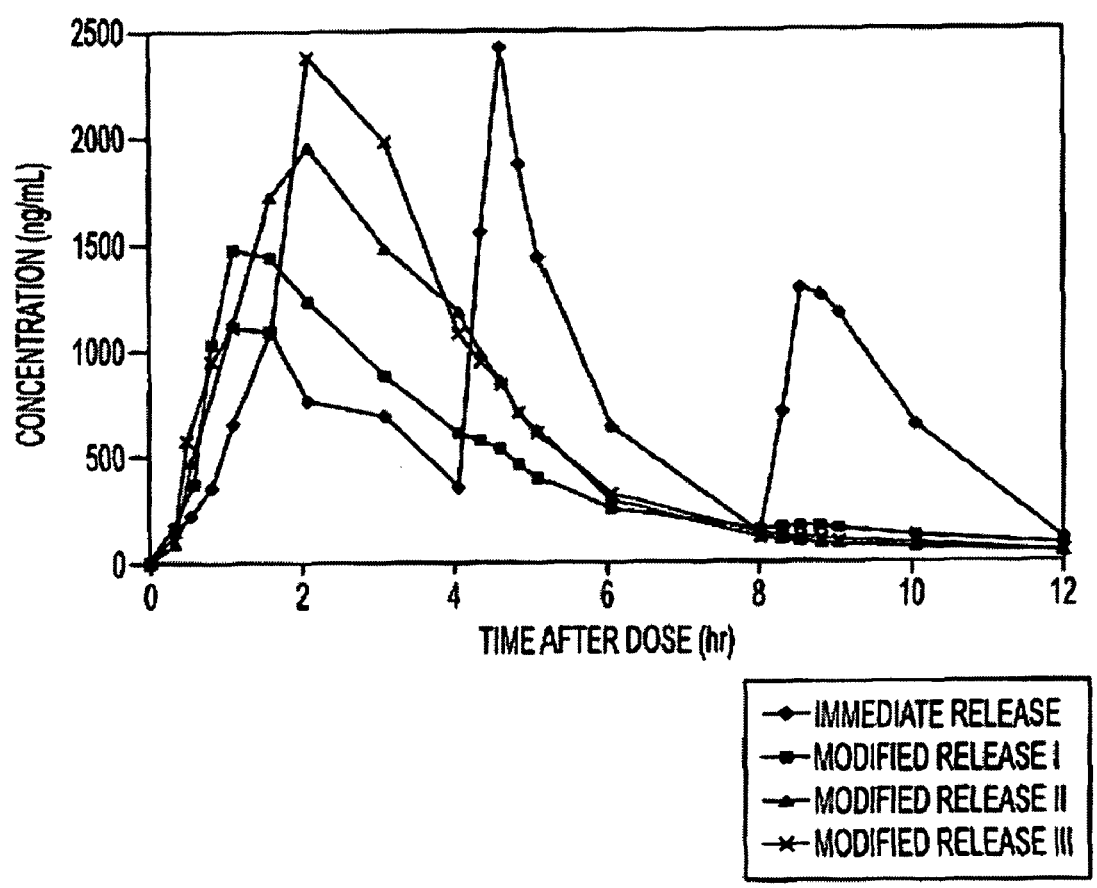
FIG. 7 is a graph demonstrating the plasma concentration of guaifenesin over time in healthy human volunteers from an immediate release tablet lot which is known in the art, a non-layered modified release tablet lot of the present invention, and two bi-layered modified release tablet lots of the present invention (one comprising 600 mg of immediate release formulation and 600 mg of sustained release formulation and the other one comprising 400 mg of immediate release formulation and 800 mg of sustained release formulation).

The plasma samples were analyzed by a fully validated HPLC method. The results are depicted in FIG. 7. This resulting plasma concentration v. time data was subjected to pharmacokinetic analysis using non-compartmental analysis with Winnonlin 1.5. The results of the pharmacokinetic parameters analysis are below.

| | Formulation | $T_{max}$ (hr.) | $C_{max}$ (ng/ml) | $AUC_{0-12}$ (hr * ng/ml) | $T_{1/2}$ (hrs.) | $AUC_{inf}$ (hr * ng/ml) |
| --- | --- | --- | --- | --- | --- | --- |
| Mean | ORGANIDIN NR | 0.90 | 2609.40 | 8768.40 | 1.28 | 9082.78 |
| Mean | SR I | 2.30 | 1631.40 | 5549.30 | 2.88 | 6044.93 |
| Mean | SR II | 2.30 | 2415.40 | 7304.38 | 1.48 | 7509.78 |
| Mean | SR III | 1.95 | 2938.00 | 8904.62 | 2.05 | 9161.03 |

Sustained Formulations II and III exhibited a $C_{max}$ more comparable to the immediate release formulation and an increased $AUC_{inf}$ from that of the non-layered Sustained Formulation I. However, the half-lives of both Sustained Formulation II and III were reduced from the half-life of Sustained Formulation I. Although these bi-layer tablets showed an improved serum concentration of guaifenesin and an increased overall concentration with time, their half-life was compromised.

Example 5

A dissolution study was run to compare dissolution profiles of Formulation I, Formulation II and Formulation III prepared as defined in Example 4 above, and Formulation IV, a bi-layer tablet lot with 200 mg IR and 1000 mg SR prepared with the following composition:
IR Formulation

| Components | Weight per Tablet |
| --- | --- |
| GUAIFENESIN DC | 211 mg |
| Microcrystalline Cellulose (AVICEL) | 118 mg |
| Sodium Starch Glycolate (EXPLOTAB) | 30 mg |
| Magnesium Stearate | 1 mg |

SR Formulation

| Components | Weight per Tablet |
| --- | --- |
| GUAIFENESIN DC | 1053 mg |
| METHOCEL E10M | 25 mg |
| CARBOPOL 974P | 12.5 mg |
| Emerald Green Lake | 3.3 mg |
| Magnesium Stearate | 5.7 mg |

Figure 8:
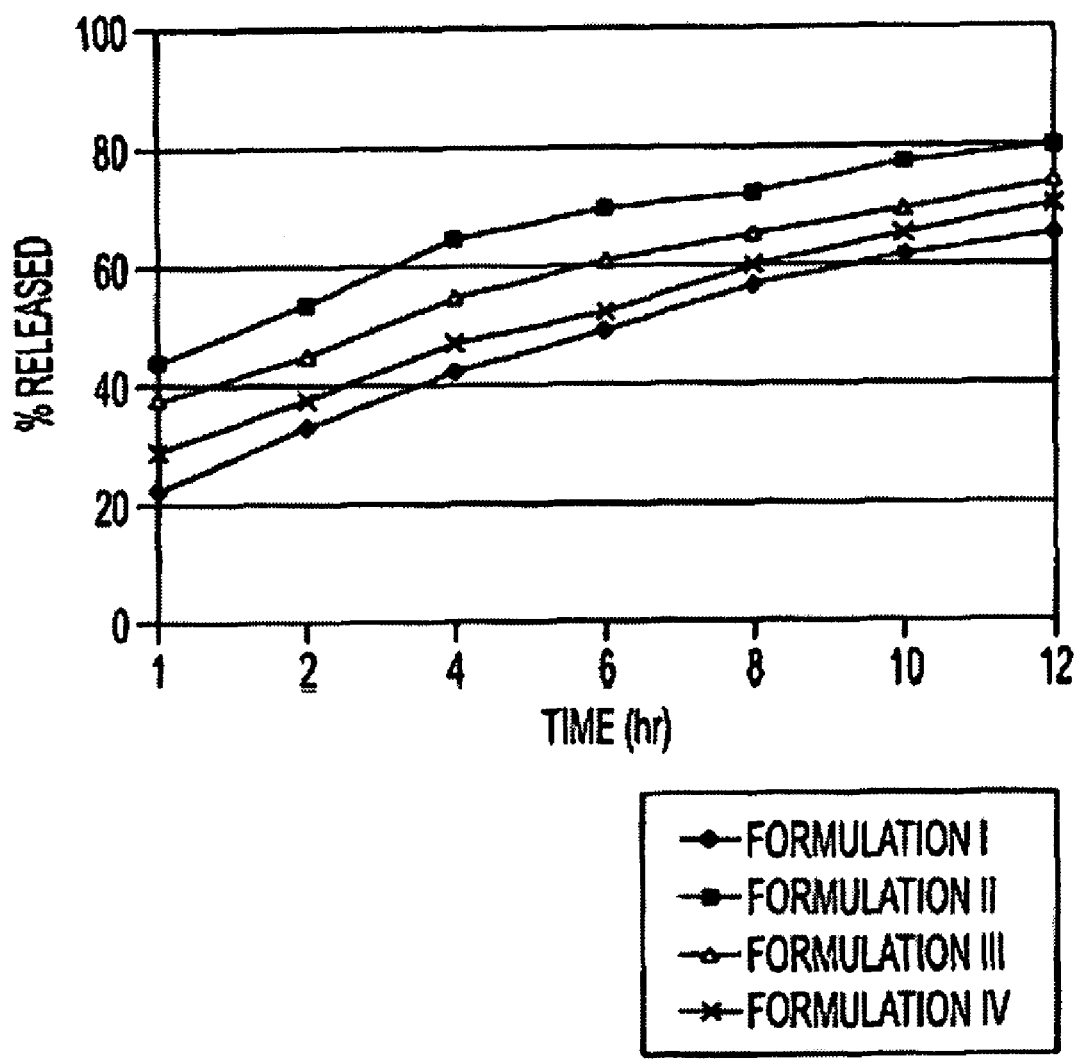
FIG. 8 is a graph demonstrating the dissolution profiles of four sustained release tablets of the present invention: one tablet is non-layered, comprising 1200 mg of sustained release formulation; another tablet is bi-layered, comprising 600 mg of sustained release formulation and 600 mg of immediate release formulation; another tablet is bi-layered, comprising 800 mg of sustained release formulation and 400 mg of immediate release formulation; and yet another tablet is bi-layered comprising 1000 mg of sustained release formulation and 200 mg of immediate release formulation.

The following is a summary of the results which are also depicted in FIG. 8.

| | Formulation I % released | Formulation II % released | Formulation III % released | Formulation IV % released |
| --- | --- | --- | --- | --- |
| 1 hr | 22 | 45 | 38 | 29 |
| 2 hr | 34 | 54 | 46 | 38 |
| 4 hr | 43 | 65 | 56 | 48 |
| 6 hr | 50 | 70 | 61 | 53 |
| 8 hr | 58 | 73 | 66 | 60 |
| 10 hr | 62 | 78 | 70 | 66 |
| 12 hr | 66 | 81 | 75 | 71 |

Formulation I, the non bi-layered tablet, demonstrated the slowest release of guaifenesin. Formulation II and Formulation III had the fastest rates of release and would, therefore, exhibit a faster rate of release and thus a shorter lived therapeutic effect in vivo. Formulation IV has a rate of release which was faster than Formulation I, comprising no immediate release blend, but slower than Formulation II and Formulation III, both comprising more immediate release blend than Formulation IV.

Example 6

The in vivo behavior of Formulation IV bi-layered tablets, prepared as described above in Example 5, was compared to an immediate release formulation (ORGANIDIN NR). The open-label, multiple dose, randomized, 2-way crossover study involved 26 healthy volunteers averaging 31.31±9.81 years of age with a range of 19 years to 50 years of age. The subjects weighed 166.77±29.83 lbs. The subjects were placed into one of two treatment groups. Group 1 received Formulation IV tablet with 240 ml of water after an overnight fast every 12 hours for 5 days and a single dose on day 6. Group 2 received 400 mg of ORGANIDIN NR (2×200 mg tablets) with 240 ml of water every 4 hours for 5 days and one 400 mg dose every four hours for a total of 3 doses on day 6.

Blood samples (5 ml with sodium heparin as anticoagulant) were taken prior to dosing on days 1, 4, 5, and 6. On Day 1, additional blood samples (5 ml with sodium heparin as anticoagulant) were also obtained at 0.5, 0.75, 1, 1.5, 2, 3, 4, 4.5, 4.75, 5, 5.5, 6, 7, 8, 8.5, 8.75, 9, 9.5, 10. 11, and 12 hours after the initial dose. On Day 6, additional blood samples (5 ml with sodium heparin as anticoagulant) were also obtained at 0.5, 0.75, 1, 1.5, 2, 3, 4, 4.5, 4.75, 5, 5.5, 6, 7, 8, 8.5, 8.75, 9, 9.5, 10, 11, 12, 14, 16, and 24 hours after the initial dose. Plasma was separated and the plasma frozen until analyzed for guaifenesin content. The resulting plasma concentration data was subjected to pharmacokinetic and statistical analysis in order to determine if the sustained release tablets performed as controlled release tablets at steady state.

The results of the pharmacokinetic parameters analysis are below.

Averaged Testing—11 Twelve-Hour Intervals

| | Formulation | $T_{max}$ (hr.) | $C_{max}$ (ng/ml) | $AUC_{0-12}$ (hr * ng/ml) | $T_{1/2}$ (hrs.) | $AUC_{inf}$ (hr * ng/ml) |
|---|---|---|---|---|---|---|
| Mean | ORGANIDIN NR | 1.69 | 2463.20 | 8381.93 | 0.78 | 8528.51 |
| Mean | Bi-layered Tablet | 1.05 | 2111.38 | 7875.68 | 3.31 | 8686.08 |

Figure 9:
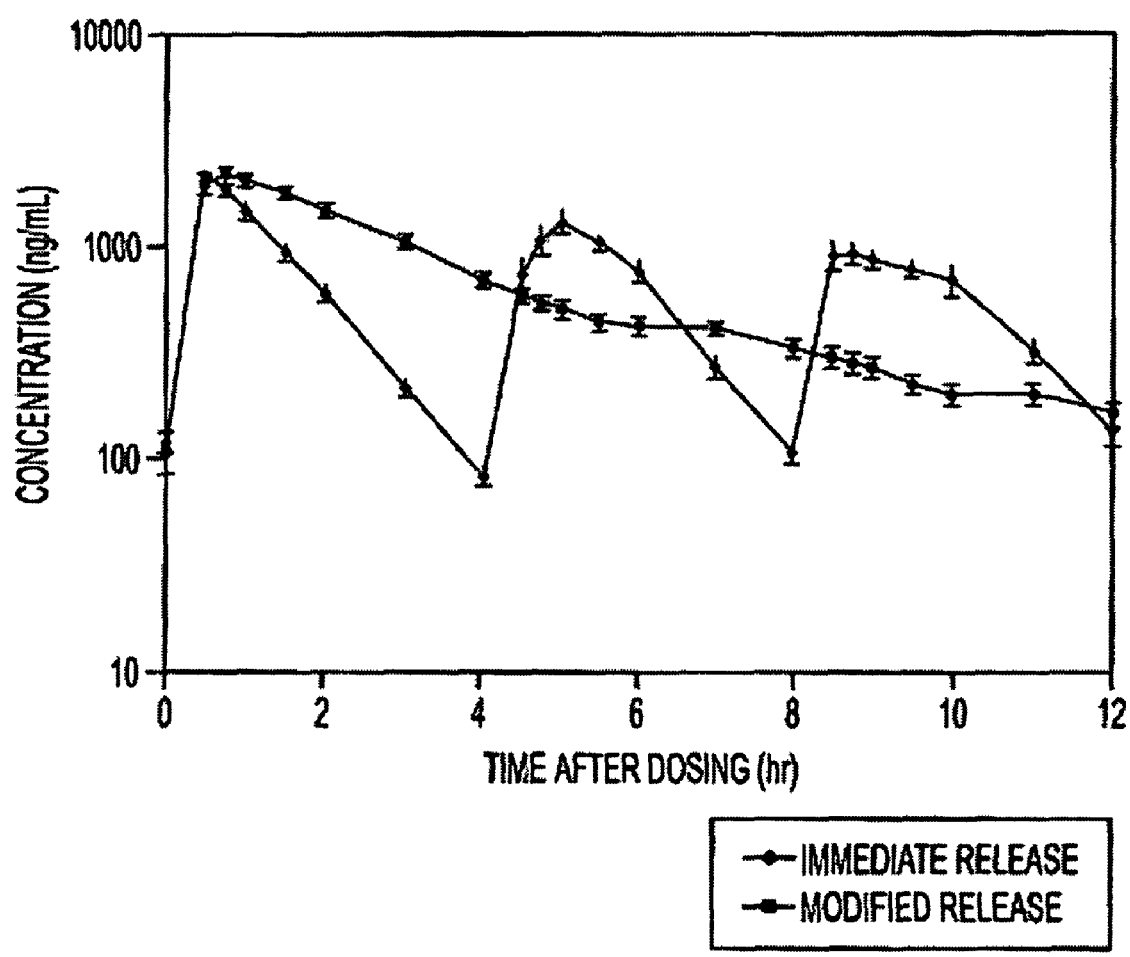
FIG. 9 is a graph demonstrating the plasma concentration of guaifenesin over an averaged 12 hour interval (taken from 11 twelve hour intervals over 5.5 days) in healthy human volunteers from an immediate release tablet lot known in the art and a bi-layered modified release tablet lot of the present invention.

The results of the testing are depicted in FIG. 9.

Steady State Testing

| | Formulation | $T_{max}$ (hr.) | $C_{max}$ (ng/ml) | $AUC_{0-12}$ (hr * ng/ml) | $T_{1/2}$ (hrs.) | $AUC_{inf}$ (hr * ng/ml) |
|---|---|---|---|---|---|---|
| Mean | ORGANIDIN NR | 2.03 | 2278.20 | 7751.23 | 0.88 | 7962.14 |
| Mean | Bi-layered Tablet | 0.86 | 2349.6 | 8202.47 | 3.61 | 9259.24 |

Figure 10:
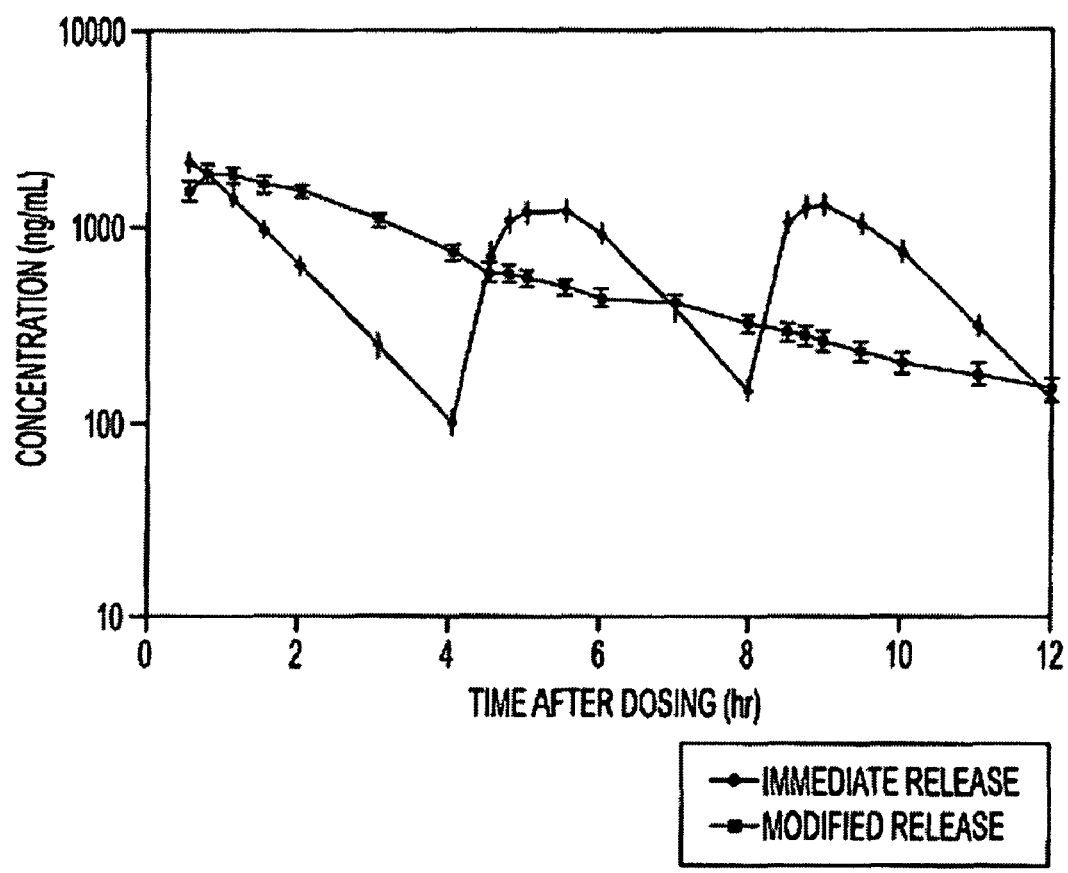
FIG. 10 is a graph demonstrating the plasma concentration of guaifenesin over time (the last twelve hour interval of the 11 twelve hour intervals described above) in healthy human volunteers from an immediate release tablet lot known in the art and a bi-layered modified release tablet lot of the present invention.

The results of the testing are depicted in FIG. 10.

The 200/1000 mg bi-layered tablet exhibited a $C_{max}$ and a $AUC_{inf}$ equivalent to that of the immediate release blend, a short $T_{max}$ and an extended half-life. Thus, a bi-layered tablet with 200 mg guaifenesin in the immediate release formulation and 1000 mg of guaifenesin in the sustained release formulation results in a tablet which delivers a high serum concentration in a short period of time, yet maintains an effective concentration of guaifenesin in the blood stream for a full twelve hours.

Example 7

A study was performed to examine the relative bioavailability of two different dosage strengths of modified release guaifenesin formulations of the present invention as well as the effect of food on the relative bioavailability of a guaifenesin formulation of the present invention in normal, healthy male and/or female volunteers. Two batches of guaifenesin bi-layer tablets, one 600 mg and one 1200 mg, were prepared according to the following composition.

600 mg Tablet

IR Formulation

| Components | Weight per 200,000 Tablets |
|---|---|
| GUAIFENESIN DC | 21.05 kg |
| Microcrystalline Cellulose (AVICEL PH102) | 11.75 kg |
| Sodium Starch Glycolate (EXPLOTAB) | 3.00 kg |
| Magnesium Stearate | 0.10 kg |

SR Formulation

| Components | Weight per 200,000 Tablets |
|---|---|
| GUAIFENESIN DC | 105.27 kg |
| Hydroxypropyl Methyl Cellulose (METHOCEL E10M) | 2.50 kg |
| Carbomer (CARBOPOL 974P) | 1.25 kg |
| FD&C Blue #1 Aluminum Lake Dye | 0.33 kg |
| Magnesium Stearate | 0.57 kg |

1200 mg Tablet

IR Formulation

| Components | Weight per 100,000 Tablets |
|---|---|
| GUAIFENESIN DC | 21.05 kg |
| Microcrystalline Cellulose (AVICEL PH102) | 11.75 kg |
| Sodium Starch Glycolate (EXPLOTAB) | 3.00 kg |
| Magnesium Stearate | 0.10 kg |

SR Formulation

| Components | Weight per 100,000 Tablets |
|---|---|
| GUAIFENESIN DC | 105.27 kg |
| Hydroxypropyl Methyl Cellulose (METHOCEL E10M) | 2.50 kg |
| Carbomer (CARBOPOL 974P) | 1.25 kg |
| FD&C Blue #1 Aluminum Lake Dye | 0.33 kg |
| Magnesium Stearate | 0.57 kg |

Note: the 600 mg and 1200 mg tablets were similarly prepared, the only difference between the dosage forms being that the 1200 mg tablet contained about twice as much of each ingredient as the 600 mg tablet.

The in vivo behaviors of a 600 mg tablet administered to volunteers in the fasting state (about 10 hours pre-dose until about 4 hours after dosing), the 1200 mg tablet administered to volunteers in the fasting state (about 10 hours pre-dose until about 4 hours after dosing), and the 1200 mg tablet administered to volunteers after a high fat meal (consumed within 30 minutes of dosing) were compared. The open-label study involved 27 healthy volunteers between the ages of 18 and 55. The subjects weighed within 15% of their Ideal Body Weight as defined by the 1983 Metropolitan Life chart. The 27 volunteers were divided into 3 treatment groups, 9 receiving the 600 mg tablet, 9 receiving the 1200 mg tablet while fasting, and 9 receiving a 1200 mg tablet after consuming a high fat meal for Period 1 of the trial. After completion of Period 1, the volunteers were crossed-over for Period 2 (e.g. so that the 9 volunteers who had been receiving the 600 mg tablet in Period 1 received the 1200 mg tablet while fasting in Period 2). After completion of Period 2, the volunteers were crossed-over again into their 3rd and final treatment group (i.e. the 9 volunteers who received the 1200 mg tablet while fasting in Period 2 and the 600 mg tablet while fasting in Period 1 received the 1200 mg tablet after consumption of a high fat meal in Period 3). Each volunteer was administered one dose of the appropriate tablet and then monitored over a 16 hour period.

Blood samples (7 ml with sodium heparin as anticoagulant) were taken about one hour prior to dosing and at specific intervals up to 16 hours after dosing (at 0.25, 0.5, 0.75, 1, 1.5, 2, 3, 4, 6, 8, 10, 12, 14, and 16 hours). All blood samples were chilled and centrifuged within 30 minutes of being drawn. The plasma was separated, transferred to a polypropylene tube, frozen at −20° C. or below and stored frozen until being shipped for guaifenesin analysis. The volunteers were then given at least a seven day washout period (where no guaifenesin was administered to them under the study) prior to being crossed-over to the next treatment group.

Figure 11:
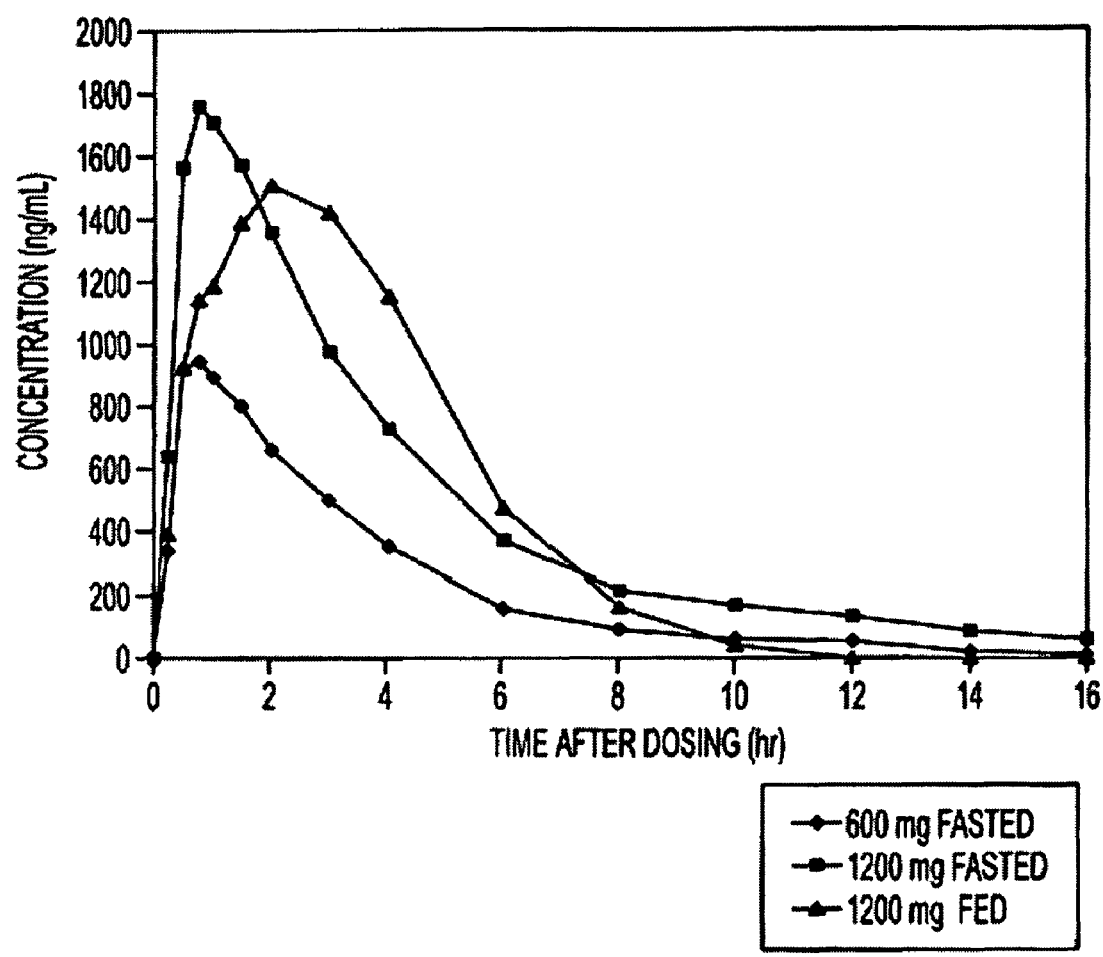
FIG. 11 is a graph demonstrating the averaged plasma concentration of guaifenesin over a 16 hour period in 27 healthy human volunteers from 600 mg bi-layered modified release tablets of the present invention administered to fasting volunteers, 1200 mg bi-layered modified release tablets of the present invention administered to fasting volunteers, and 1200 mg bi-layered modified release tablets of the present invention administered to volunteers who had been fed a high fat meal.

The plasma samples were analyzed by a fully validated HPLC method. The results are depicted in FIG. 11. This resulting plasma concentration v. time data was subjected to pharmacokinetic analysis using non-compartmental analysis with Winnonlin 1.5. The results of the pharmacokinetic parameters analysis are below.

|  | Formulation | $T_{max}$ (hr.) | $C_{max}$ (ng/ml) | $AUC_{0-12}$ (hr * ng/ml) | $T_{1/2}$ (hrs.) | $AUC_{inf}$ (hr * ng/ml) |
|---|---|---|---|---|---|---|
| Mean | 600 mg Fasted | 0.81 | 1074.26 | 3623.03 | 2.33 | 3676.23 |
| Mean | 1200 mg Fasted | 0.94 | 1948.62 | 7483.20 | 3.33 | 7912.61 |
| Mean | 1200 mg Fed | 2.18 | 1988.08 | 7424.20 | 0.91 | 7425.29 |

The 600 mg tablet demonstrated a serum profile approximately directly proportional to the serum profile of the 1200 mg tablet. The $C_{max}$ of the 600 mg tablet was about 55% that of the 1200 mg tablet. The $AUC_{0-12}$ of the 600 mg tablet was about 48% that of the 1200 mg tablet and the $AUC_{inf}$ of the 600 mg tablet was about 46% that of the 1200 mg. improved serum concentration of guaifenesin and an increased overall concentration with time, their half-life was compromised.

The 1200 mg tablet demonstrated that the bi-layer tablets of this invention greatly reduce the food effect in bioavailability and serum concentration of guaifenesin. The $C_{max}$ of the 1200 mg tablet administered after a high fat meal (fed tablet) was about 102% of the $C_{max}$ of the 1200 mg tablet administered after fasting (fasted tablet). The $AUC_{0-12}$ of the 1200 mg fed tablet was about 99% that of the fasted tablet and the $AUC_{inf}$ of the 1200 mg fed tablet was about 94% that of the fasted tablet.

Example 8

Two batches of guaifenesin/dextromethorphan HBr bi-layer tablets, one 600 mg and one 1200 mg, were prepared according to the following composition. In the 30 mg dextromethorphan tablet 7.5 mg was within the immediate release layer and 22.5 mg within the modified release layer.

600 mg Guaifenesin/30 mg Dextromethorphan Tablet

Sustained Release (SR) Formulation

| Components | Weight per 200,000 tablets (kg) |
|---|---|
| Guaifenesin, USP | 101.00 |
| Dextromethorphan HBr | 4.50 |
| CARBOPOL 974P, NF | 1.50 |
| Microcrystalline Cellulose (METHOCEL E10M) | 5.00 |
| D&C YELLOW # 10 Aluminum Lake (14-18%) | 0.04 |
| Magnesium Stearate | 1.00 |

Immediate Release (IR) Formulation

| Components | Weight per 480,000 tablets (kg) |
|---|---|
| Guaifenesin, USP | 45.60 |
| Dextromethorphan HBr | 3.60 |
| Sodium Starch Glycolate, NF (Explotab) | 3.60 |
| Microcrystalline Cellulose (AVICEL PH102) | 40.32 |
| METHOCEL E10M, USP | 2.40 |
| Magnesium Stearate, NF | 0.48 |

1200 mg Guaifenesin/60 mg Dextromethorphan HBr Tablet

SR Layer Formulation

| Components | Weight per 100,000 tablets (kg) |
|---|---|
| Guaifenesin | 101.00 |
| Dextromethorphan HBr | 4.50 |
| Microcrystalline Cellulose (METHOCEL E10M) | 5.00 |
| CARBOPOL 974P, NF | 1.50 |
| FD&C Blue No. 1 Aluminum Lake (11-13%) | 0.04 |
| Magnesium Stearate | 1.0 |

IR Layer Formulation

| Components | Weight per 240,000 tablets (kg) |
|---|---|
| Guaifenesin | 45.60 |
| Dextromethorphan HBr | 3.60 |
| Sodium Starch Glycolate, NF (Explotab) | 3.60 |
| Microcrystalline Cellulose (AVICEL PH102) | 40.32 |
| METHOCEL E10M, USP | 2.40 |
| Magnesium Stearate, NF | 0.48 |

Figure 12:
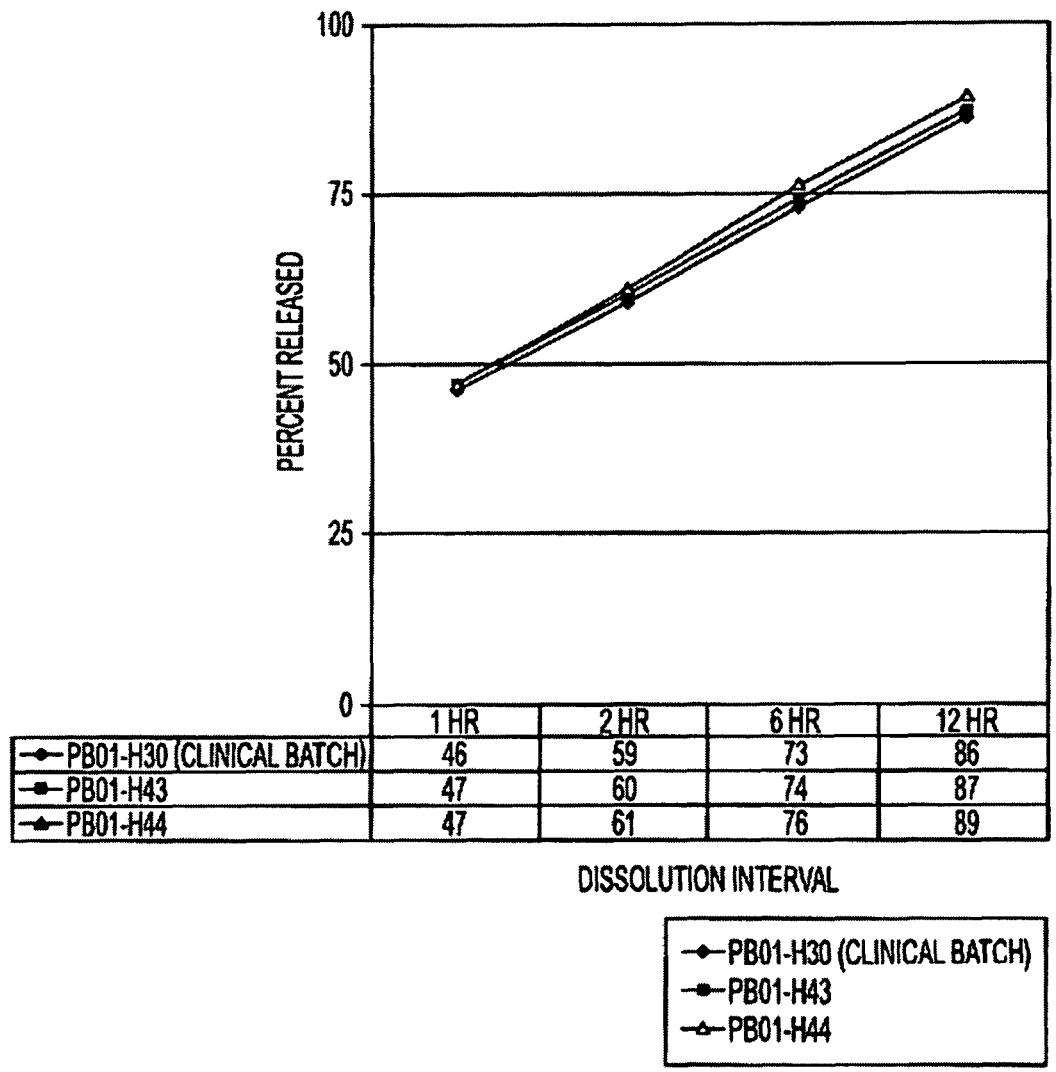
FIG. 12 is a graph demonstrating the dissolution profile of dextromethorphan HBr as measured by three different batches of a 1200 mg guaifenesin-60 mg dextromethorphan tablet over a 12 hour period as measured by the weight percentage of dextromethorphan HBr dissolved over time.

The following is a summary of the dextromethorphan HBr Dissolution Rate of the 1200 mg guaifenesin-60 mg dextromethorphan tablet results which are also depicted in FIG. 12.

|       | Formulation I<br>% released | Formulation II<br>% released | Formulation III<br>% released |
|-------|------------------------------|-------------------------------|--------------------------------|
| 1 hr  | 46 | 47 | 47 |
| 2 hr  | 59 | 60 | 61 |
| 6 hr  | 73 | 74 | 76 |
| 12 hr | 86 | 87 | 89 |

The in vivo behavior of the 1200 mg guaifenesin and 60 mg tablet was studied by measuring the plasma concentration of guaifenesin, dextromethorphan HBr, and the metabolite dextrorphan. FIGS. 13-15 illustrate the plasma concentration for each drug or metabolite in two formulations, Formulation B and Formulation C, during a 24 hour period. Immediately after administration the plasma concentration of guaifenesin peaks in about an hour, followed by a gradual plasma concentration decrease over 24 hours. Immediately after administration, guaifenesin plasma concentration never decreased to less than 200 ng/ml over 12 hours. Thereafter, guaifenesin plasma concentration gradually decreased over the next 12 hours. Plasma concentration of dextromethorphan HBr peaks at about 6 hours at about 12 ng/ml and the concentration is maintained for the following 19 hours.

Example 9

A study was performed to examine the relative bioavailability of a sustained release guaifenesin with dextromethorphan formulation of the present invention with normal, healthy male and/or female volunteers. A batch of guaifenesin and dextromethorphan bi-layer tablet, 1200 mg, was prepared according to the composition described above for Example 8.

The in vivo behaviors of the 1200 mg tablet administered to volunteers in the fasting state (about 10 hours pre-dose until about 4 hours after dosing) was determined. The open-label study involved 29 healthy volunteers between the ages of 18 and 55. The subjects weighed within 15% of their Ideal Body Weight as defined by the 1983 Metropolitan Life chart. The 29 volunteers were divided into two treatment groups half receiving the 1200 mg tablet while fasting for Period 1 of the trial. Each volunteer was administered one dose of the appropriate tablet and then monitored over a 16 hour period.

Blood samples (7 ml with sodium heparin as anticoagulant) were taken about one hour prior to dosing and at specific intervals up to 16 hours after dosing (at 0.25, 0.5, 0.75, 1, 1.5, 2, 3, 4, 6, 8, 10, 12, 14, and 16 hours). All blood samples were chilled and centrifuged within 30 minutes of being drawn. The plasma was separated, transferred to a polypropylene tube, frozen at −20° C. or below and stored frozen until being shipped for guaifenesin and dextromethorphan analysis.

The plasma samples were analyzed by a fully validated HPLC method by PPD Development (3230 Deming Way Suite 190, Middleton, Wis. 53562). The resulting plasma concentration v. time data was subjected to pharmacokinetic analysis using non-compartmental analysis with Winnonlin 1.5. The results of the pharmacokinetic parameters analysis for guaifenesin include a $T_{max}$ of 1.48 hr, $C_{max}$ (ng/ml) of 2196, $AUC_{0-12}$ (hr*ng/ml) of 8702, $T_{1/2}$ of 1.32 hrs., and an $AUC_{inf}$(hr*ng/ml) of 8732.5. The results of the pharmacokinetic parameters analysis for dextromethorphan include a $T_{max}$ of 5.0 hrs, $C_{max}$ (pg/ml) of 5157, $AUC_{0-12}$ (hr*pg/ml) of 74209, $T_{1/2}$ of 7.93 hrs., and an $AUC_{inf}$(hr*pg/ml) of 75016.

Example 10

Two batches of guaifenesin-pseudoephedrine HCl bi-layer tablets, one 600 mg and one 1200 mg, were prepared according to the following composition.

600 mg Guaifenesin/60 mg Pseudoephedrine HCl Tablet

SR Layer Formulation

| Components | Weight per 300,000 tablets (kg) |
|---|---|
| Guaifenesin DC (95%) | 157.90 |
| Pseudoephedrine HCl | 18.0 |
| Hydroxypropyl Methylcellulose (METHOCEL E10M) | 4.50 |
| CARBOPOL 974P, NF | 2.25 |
| FD&C Yellow No. 6 Aluminum Lake (15-18%) | 0.24 |
| Magnesium Stearate | 1.50 |

IR Layer Formulation

| Components | Weight per 300,000 tablets (kg) |
|---|---|
| Guaifenesin DC (95%) | 39.476 |
| Microcrystalline Cellulose (AVICEL PH102) | 22.028 |
| Sodium Starch Glycolate | 5.626 |
| Magnesium Stearate, NF | 0.188 |

1200 mg Guaifenesin/120 mg Pseudoephedrine HCl Tablet

SR Layer Formulation

| Components | Weight per 150,000 tablets (kg) |
|---|---|
| Guaifenesin DC (95%) | 157.89 |
| Pseudoephedrine HCl | 18.00 |
| Hydroxypropyl Methylcellulose (METHOCEL E10M) | 4.50 |
| CARBOPOL 974P, NF | 2.25 |
| FD&C Red No. 40 Aluminum Lake (14-16%) | 0.06 |
| Magnesium Stearate | 1.50 |

IR Layer Formulation

| Components | Weight per 150,000 tablets (kg) |
|---|---|
| Guaifenesin DC (95%) | 39.476 |
| Microcrystalline Cellulose (AVICEL PH102) | 22.028 |
| Sodium Starch Glycolate | 5.626 |
| Magnesium Stearate, NF | 0.188 |

Figure 16:
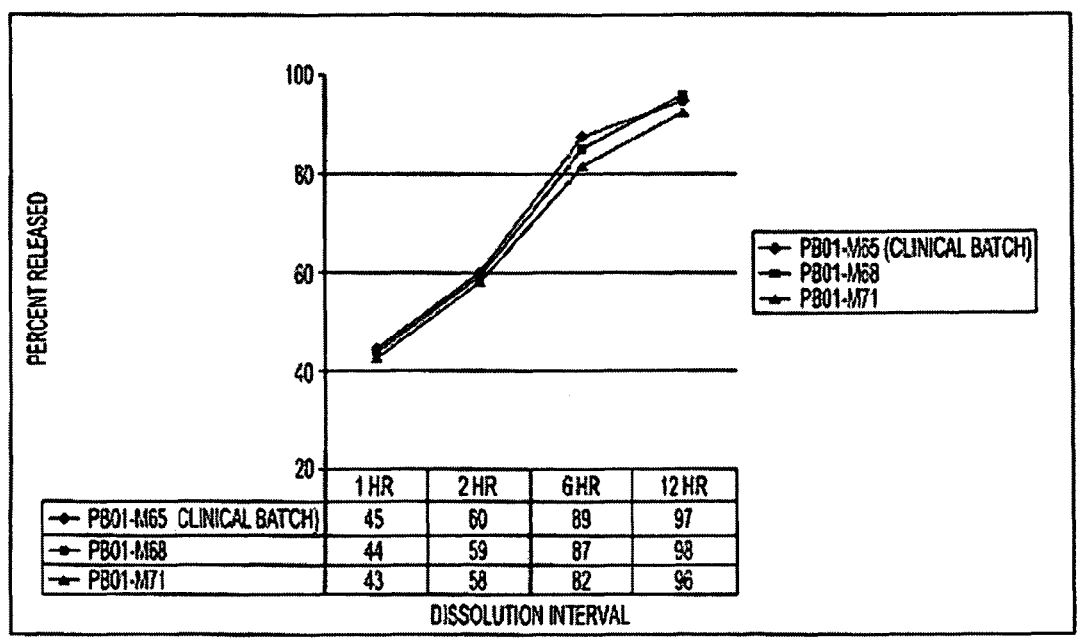
FIG. 16 is a graph demonstrating the dissolution profile of pseudoephedrine HCl in three different batches of a 1200 mg guaifenesin-120 mg pseudoephedrine HCl tablet formulation over a 12 hour period as measured by the percent pseudoephedrine HCl dissolved over time.

The following is a summary of the pseudoephedrine Dissolution Rate of the 1200 mg guaifenesin-60 mg pseudoephedrine tablet results which are also depicted in FIG. 16.

|  | Formulation I<br>% released | Formulation II<br>% released | Formulation III<br>% released |
|---|---|---|---|
| 1 hr | 45 | 44 | 43 |
| 2 hr | 60 | 59 | 58 |
| 6 hr | 89 | 87 | 82 |
| 12 hr | 97 | 98 | 96 |

The in vivo behavior of the 1200 mg guaifenesin and 120 mg pseudoephedrine tablet was studied by measuring the plasma concentration of guaifenesin, and pseudoephedrine HCl. FIGS. 17-18 illustrate the plasma concentration for each drug (Formulation B and Formulation C) during a 24 hour period. Immediately after administration the plasma concentration of guaifenesin peaks in about an hour, followed by a gradual plasma concentration decrease over 24 hours. Immediately after administration, guaifenesin plasma concentration never decreased below 200 ng/ml over 12 hours. Thereafter, guaifenesin plasma concentration gradually decreased over the next 12 hours. Plasma concentration of pseudoephedrine HCl peaked at about 6 hours and gradually decreased over the next 18 hours. The plasma concentration of pseudoephedrine HCl never decreased to less than 50 ng/ml after 30 minutes of administration.

Example 11

A study was performed to examine the relative bioavailability of sustained release guaifenesin with pseudoephedrine formulations of the present invention in normal, healthy male and/or female volunteers. A batch of guaifenesin and pseudoephedrine bi-layer tablets, 1200 mg, was prepared according to the composition described above for Example 10.

The in vivo behaviors of a 1200 mg tablet administered to volunteers in the fasting state (about 10 hours pre-dose until about 4 hours after dosing) were compared. The open-label study involved 29 healthy volunteers between the ages of 18 and 55. The subjects weighed within 15% of their Ideal Body Weight as defined by the 1983 Metropolitan Life chart. The 29 volunteers were divided into two treatment groups, half receiving the 1200 mg tablet while fasting for Period 1 of the trial. Each volunteer was administered one dose of the appropriate tablet and then monitored over a 16 hour period.

Blood samples (7 ml with sodium heparin as anticoagulant) were taken about one hour prior to dosing and at specific intervals up to 16 hours after dosing (at 0.25, 0.5, 0.75, 1, 1.5, 2, 3, 4, 6, 8, 10, 12, 14, and 16 hours). All blood samples were chilled and centrifuged within 30 minutes of being drawn. The plasma was separated, transferred to a polypropylene tube, frozen at −20° C. or below and stored frozen until being shipped for guaifenesin and pseudoephedrine analysis.

The plasma samples were analyzed by a fully validated HPLC method by PPD Development (3230 Deming Way Suite 190, Middleton, Wis. 53562). The resulting plasma concentration v. time data was subjected to pharmacokinetic analysis using non-compartmental analysis with WinnonlinF 1.5. The results of the pharmacokinetic parameters analysis for guiafenesin include a $T_{max}$ of 1.48 hr, $C_{max}$ (ng/ml) of 2196, $AUC_{0-12}$ (hr*ng/ml) of 8702, $T_{1/2}$ of 1.32 hrs., and an $AUC_{inf}$ (hr*ng/ml) of 8732.5. The results of the pharmacokinetic parameters analysis for pseudoephedrine include a $T_{max}$ of 6 hrs, $C_{max}$ (ng/ml) of 300, $AUC_{0-12}$ (hr*ng/ml) of 4201, $T_{1/2}$ of 5.98 hrs., and an $AUC_{inf}$ (hr*ng/ml) of 4709.

Other embodiments and uses of the invention will be apparent to those of skill in the art from consideration of the specification and practice of the invention disclosed herein. The specification and examples should be considered exemplary only with the true scope and spirit of the invention indicated by the following claims. As will be easily understood by those of skill in the art, variations and modifications of each of the disclosed embodiments can be easily made within the scope of this invention as defined by the following claims.

What is claimed is:

1. A drug product comprising guaifenesin and at least one additional drug, and having two portions,
    wherein a first portion comprises guaifenesin in an immediate release form, which releases guaifenesin in a human's stomach, and a second portion comprises guaifenesin in a sustained release form,
    wherein the drug product contains 1200 mg of guaifenesin and provides a mean $C_{max}$ and at least one of a mean $AUC_{inf}$ and a mean $AUC_{0-12}$ for guaifenesin under fasted conditions based on single-dose administration that are from 80% to 125% of the mean $C_{max}$ and at least one of the mean $AUC_{inf}$ and the mean $AUC_{0-12}$ for guaifenesin provided by a bi-layer tablet containing 1200 mg of guaifenesin and having an immediate release layer consisting essentially of about 210.5 mg of guaifenesin dc, about 117.5 mg of microcrystalline cellulose, about 30 mg of sodium starch glycolate, and about 1 mg of magnesium stearate, and a sustained release layer consisting essentially of about 1052.7 mg of guaifenesin dc, about 25 mg of hydroxypropyl methyl cellulose, about 12.5 mg of carbomer 934P, about 5.7 mg of magnesium stearate, and a colorant, and
    wherein guaifenesin is absorbed into bloodstream such that the drug product can be appropriately dosed once in a 12-hour period.

2. The drug product according to claim 1, wherein the mean $C_{max}$ and at least one of the mean $AUC_{inf}$ and the mean $AUC_{0-12}$ for guaifenesin provided by the drug product are from 80% to 125% of the mean $C_{max}$ and at least one of the mean $AUC_{inf}$ and the mean $AUC_{0-12}$ for guaifenesin provided by the bi-layer tablet at a 90% confidence interval.

3. The drug product according to claim 1, wherein the at least one additional drug is dextromethorphan hydrobromide, codeine, hydrocodone, phenylephrine hydrochloride, phenylpropanolamine hydrochloride, pseudoephedrine hydrochloride, ephedrine, chlorpheniramine maleate, brompheniramine maleate, phenindamine tartrate, pyrilamine maleate, doxylamine succinate, phenyltoloxamine citrate, diphenhydramine hydrochloride, promethazine, clemastine fumerate, acetaminophen, aspirin, ibuprofen, naprosin, or combinations thereof.

4. The drug product according to claim 3, wherein the at least one additional drug is dextromethorphan hydrobromide, pseudoephedrine hydrochloride, or a combination thereof.

5. The drug product according to claim 3, wherein the at least one additional drug is codeine.

6. The drug product according to claim 1, wherein the first and second portions are discrete.

7. A drug product comprising guaifenesin and at least one additional drug, and having two portions,
    wherein a first portion comprises guaifenesin in an immediate release form, which releases guaifenesin in a human subject's stomach, and a second portion comprises guaifenesin in a sustained release form,
    wherein the drug product contains 600 mg of guaifenesin and provides a mean $C_{max}$ and at least one of a mean $AUC_{inf}$ and a mean $AUC_{0-12}$ for guaifenesin under fasted conditions based on single-dose administration that are from 80% to 125% of the mean $C_{max}$ and at least one of the mean $AUC_{inf}$ and the mean $AUC_{0-12}$ for guaifenesin provided by a bi-layer tablet containing 600 mg of guaifenesin and having an immediate release layer consisting essentially of about 105.25 mg of guaifenesin dc, about 58.75 mg of microcrystalline cellulose, about 15 mg of sodium starch glycolate, and about 0.5 mg of magnesium stearate, and a sustained release layer consisting essentially of about 526.35 mg of guaifenesin dc, about 12.5 mg of hydroxypropyl methyl cellulose, about 6.25 mg of carbomer 934P, about 2.85 mg of magnesium stearate, and a colorant, and wherein guaifenesin is absorbed into bloodstream such that the drug product can be appropriately dosed once in a 12-hour period.

8. The drug product according to claim 7, wherein the mean $C_{max}$ and at least on of the mean $AUC_{inf}$ and the mean $AUC_{0-12}$ for guaifenesin provided by the drug product are from 80% to 125% of the mean $C_{max}$ and at least one of the mean $AUC_{inf}$ and the mean $AUC_{0-12}$ for guaifenesin provided by the bi-layer tablet at a 90% confidence interval.

9. The drug product according to claim 7, wherein the at least one additional drug is dextromethorphan hydrobromide, codeine, hydrocodone, phenylephrine hydrochloride, phenylpropanolamine hydrochloride, pseudoephedrine hydrochloride, ephedrine, chlorpheniramine maleate, brompheniramine maleate, phenindamine tartrate, pyrilamine maleate, doxylamine succinate, phenyltoloxamine citrate, diphenhydramine hydrochloride, promethazine, clemastine fumerate, acetaminophen, aspirin, ibuprofen, naprosin, or combinations thereof.

10. The drug product according to claim 9, wherein the at least one additional drug is dextromethorphan hydrobromide, pseudoephedrine hydrochloride, or a combination thereof.

11. The drug product according to claim 9, wherein the at least one additional drug is codeine.

12. The drug product according to claim 7, wherein the first and second portions are discrete.

* * * * *